US010266520B2

(12) United States Patent
Zimmerman et al.

(10) Patent No.: US 10,266,520 B2
(45) Date of Patent: Apr. 23, 2019

(54) BISAMIDINIUM-BASED INHIBITORS FOR THE TREATMENT OF MYOTONIC DYSTROPHY

(71) Applicant: The Board of Trustees of the University of Illinois, Urbana, IL (US)

(72) Inventors: Steven C. Zimmerman, Champaign, IL (US); Long M. Luu, Urbana, IL (US); Lien T. T. Nguyen, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 94 days.

(21) Appl. No.: 15/502,474

(22) PCT Filed: Aug. 10, 2015

(86) PCT No.: PCT/US2015/044526
§ 371 (c)(1),
(2) Date: Feb. 7, 2017

(87) PCT Pub. No.: WO2016/023039
PCT Pub. Date: Feb. 11, 2016

(65) Prior Publication Data
US 2018/0215736 A1    Aug. 2, 2018

Related U.S. Application Data

(60) Provisional application No. 62/034,932, filed on Aug. 8, 2014.

(51) Int. Cl.
*C07D 403/14* (2006.01)
*C07D 403/12* (2006.01)
*C07D 401/12* (2006.01)
*C07D 401/14* (2006.01)
*A61P 21/00* (2006.01)

(52) U.S. Cl.
CPC ............ *C07D 403/14* (2013.01); *A61P 21/00* (2018.01); *C07D 401/12* (2013.01); *C07D 401/14* (2013.01); *C07D 403/12* (2013.01)

(58) Field of Classification Search
None
See application file for complete search history.

(56) References Cited

U.S. PATENT DOCUMENTS

| 5,834,451 | A  | 11/1998 | Ohsawa et al. |
| 6,987,123 | B2 | 1/2006  | Lohray et al. |
| 7,589,123 | B2 | 9/2009  | Rees et al. |
| 7,704,951 | B2 | 4/2010  | Hirashima et al. |
| 8,754,084 | B2 | 6/2014  | Zimmerman et al. |
| 2008/0227213 | A1 | 9/2008 | Disney |
| 2010/0323993 | A1 | 12/2010 | Berglund et al. |

OTHER PUBLICATIONS

Arambula, J. F., et al., "A Simple Ligand that Slectively Targets CUG Trinucleotide Repeats and Inhibits MBNL Protein Binding," PNAS, 2009, 16068-16073, 106.
David, Arnaud, et al., "DNA Mismatch-Specific Base Flipping by a Bisacridine Macrocycle," ChemBioChem, 2003, 1326-1331, 4.
Gareiss, Peter C., et al., "Dynamic Combinatorial Selection of Molecules Capable of Inhibiting the (CUG) Repeat RNA-MBNL1 Interaction In Vitro: Discovery of Lead Compounds Targeting Myotonic Dystrophy(DM1)," JACS, 2008, 16254-16261, 130.
International Search Report and Written Opinion of the ISA/US dated Nov. 19, 2015 in International Application No. PCT/US2015/044526; 8pgs.
Jahromi, A.H., et al., "A Novel CUGexp•MBNL1 Inhibitor with Therapeutic Potential for Myotonic Dystrophy Type 1," Chemical Biology, 2013, 1037-1043, 8.
Jahromi, A.H., et al., "Developing Bivalent Ligands to Target CUG Triplet Repeats, the Causative Agent of Myotonic Dystrophy Type 1," Journal of Medicinal Chemistry, 2013, 9471-9481, 56.
Jahromi, A.H., et al., "Single-molecule Study of the CUG Repeat-MBNL1 Interaction and its Inhibition by Small Molecules," Nucleic Acids Res.; 41(13)687-6697, Jul. 2014.
Mooers, B.H., et al., "The Structural Basis of Myotonic Dystrophy from the Crystal Structure of CUG Repeats," PNAS, 2005, 16626-16631, 102.
Wong, Chun-Ho, "Discovery of Small Molecule Inhibitors of MBNL • RNA Interaction: Toward Therapeutic Agents to Treat Myotonic Dystrophy," The Chinese University of Hong Kong (Presentation), 2012, 9 pages.
Wong, Chun-Ho, et al., "Selective Inhibition of MBNL1—CCUG Interaction by Small Molecules Toward Potential Therapeutic Agents for Myotonic Dystrophy Type 2 (DM2)," Nucleic Acids Research, 2011, 8881-8890, 39.
Wong, Chun-Ho, et al., "Targeting Toxic RNAs that Cause Myotonic Dystrophy Type 1 (DM1) with a Bisamidinium Inhibitor," JACS, 2014; 6355-6361; 136.

*Primary Examiner* — Samantha L Shterengarts
(74) *Attorney, Agent, or Firm* — Haukaas Fortius PLLC; Michael H. Haukaas

(57) ABSTRACT

The invention provides compounds, compositions and therapeutic methods. The compounds and compositions can be used for the treatment of myotonic dystrophy. The compounds can selectively bind to CUG repeats in RNA, or to CTG repeats in DNA, and inhibit replication of the nucleic acids. RNA-targeted therapeutic agents for the treatment of myotonic dystrophy type 1 (DM1) are described. In one embodiment, two bisamidinium ligands are linked using "click" chemistry to form a heterodimer that is a potent inhibitor of the MBNL1-rCUG$^{exp}$ complex ($K_I$=25±8 nM), is relatively non-toxic to HeLa cells, dissolves nuclear foci, corrects >80% of the IR misregulated alternative splicing in DM1 model cells (1 μM), and shows improvement of disease phenotypes in a DM1 *Drosophila* model.

22 Claims, 9 Drawing Sheets

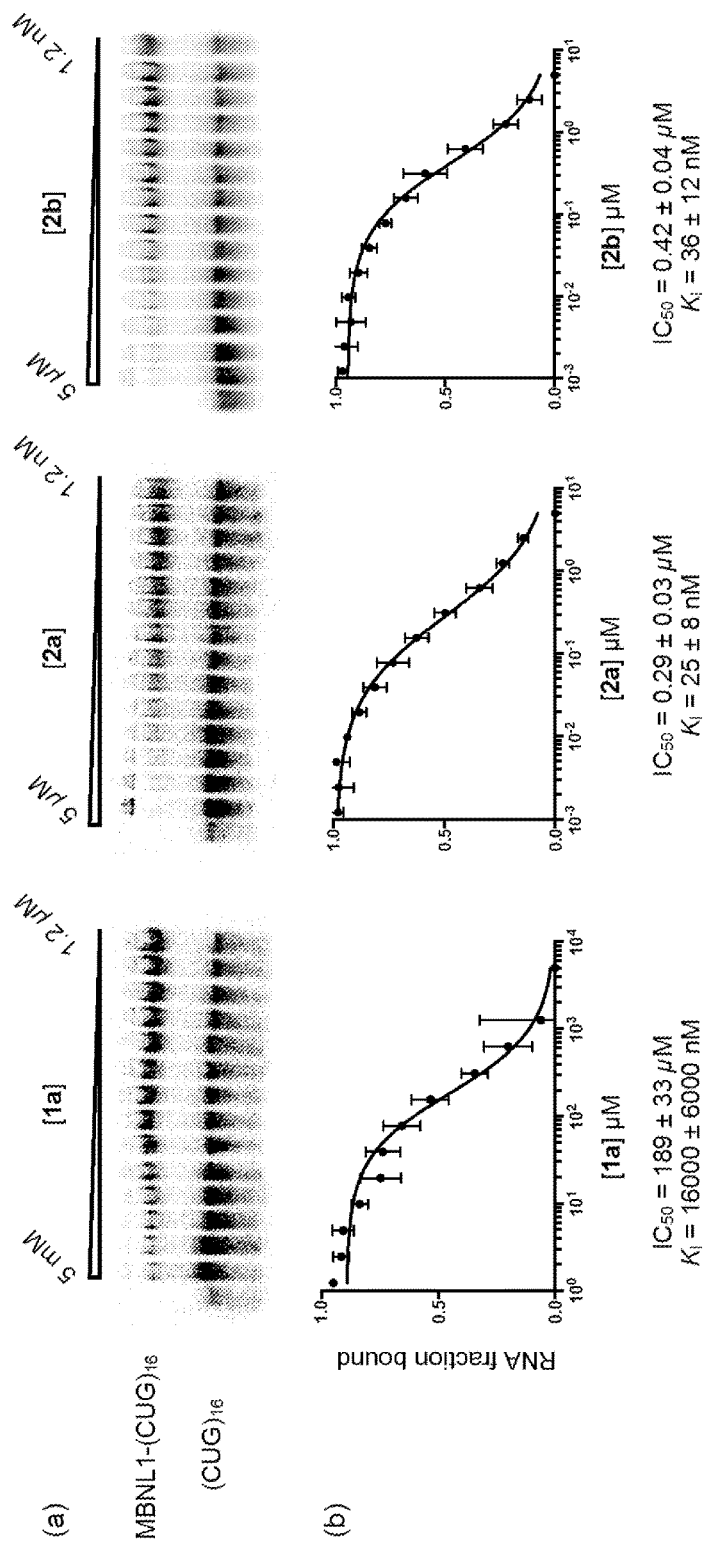
Fig. 1A-B

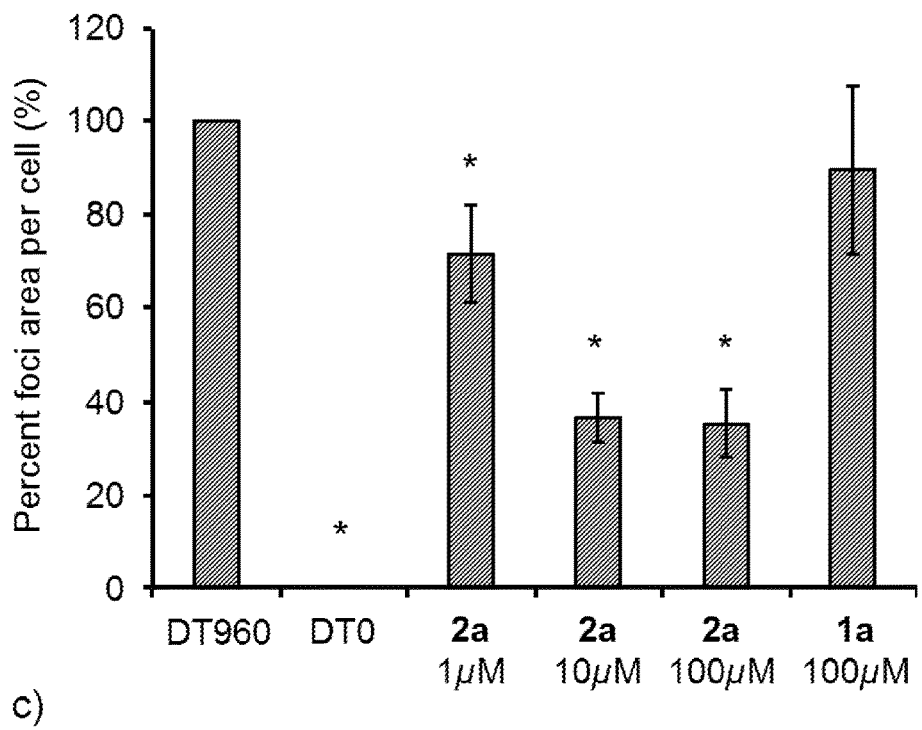
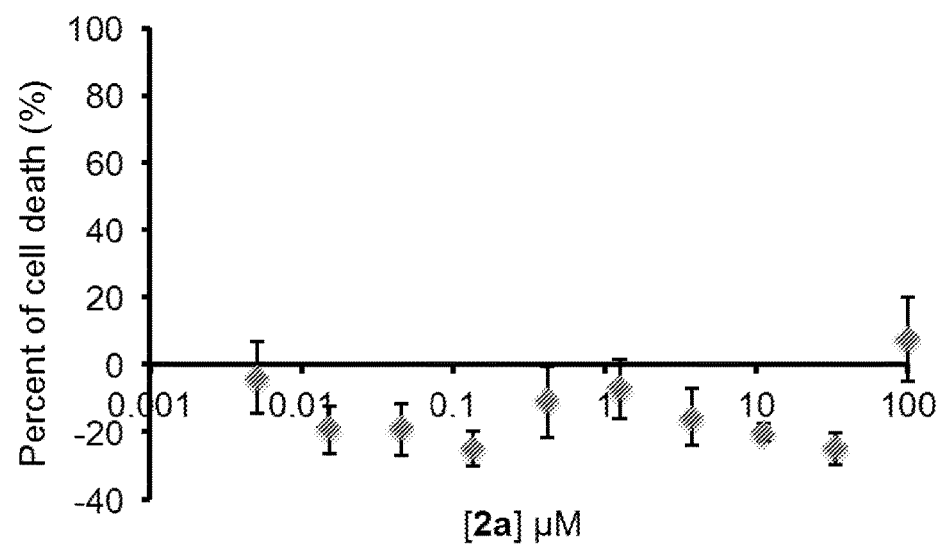
*Fig. 2B-C*

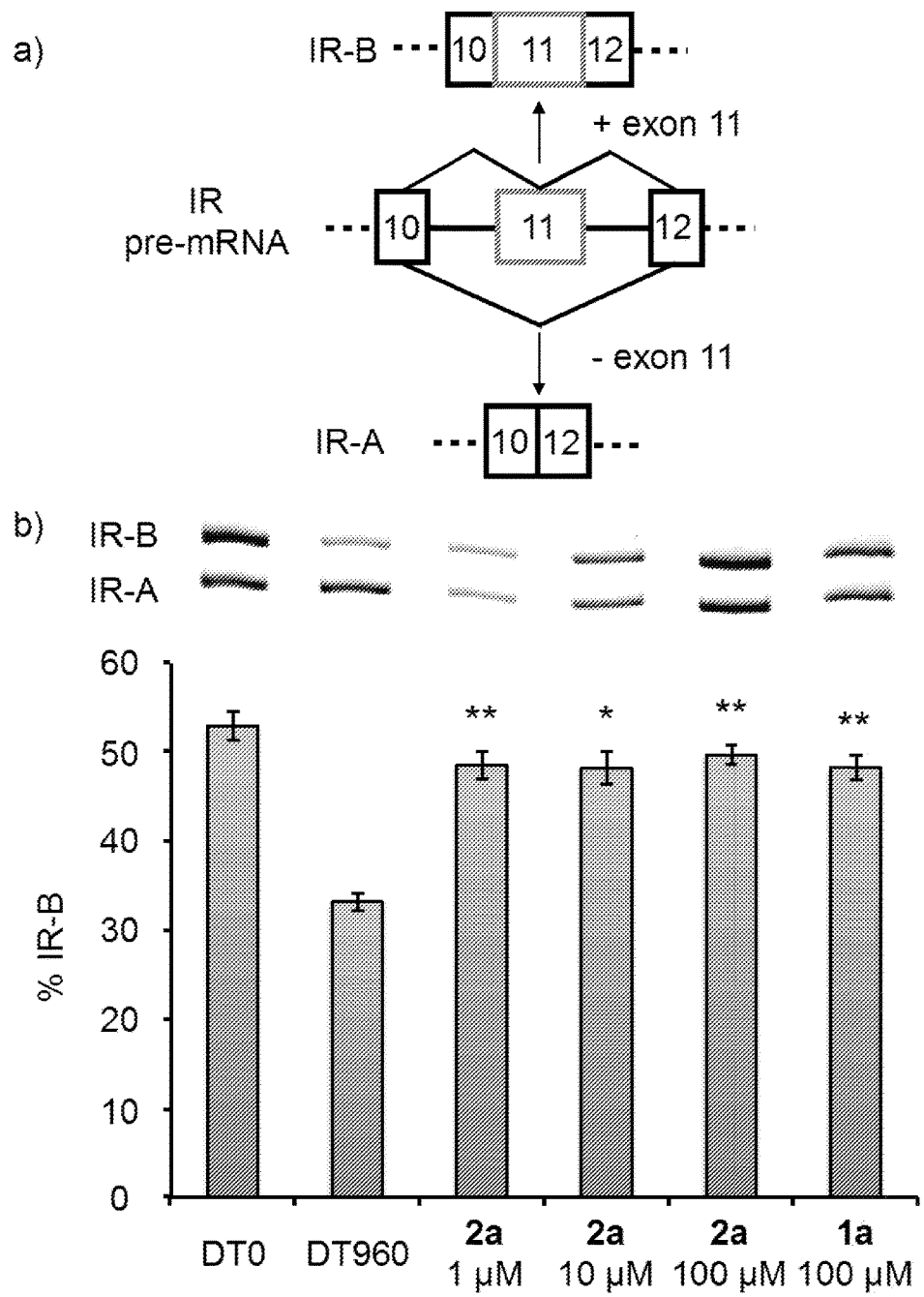
Fig. 3A-B

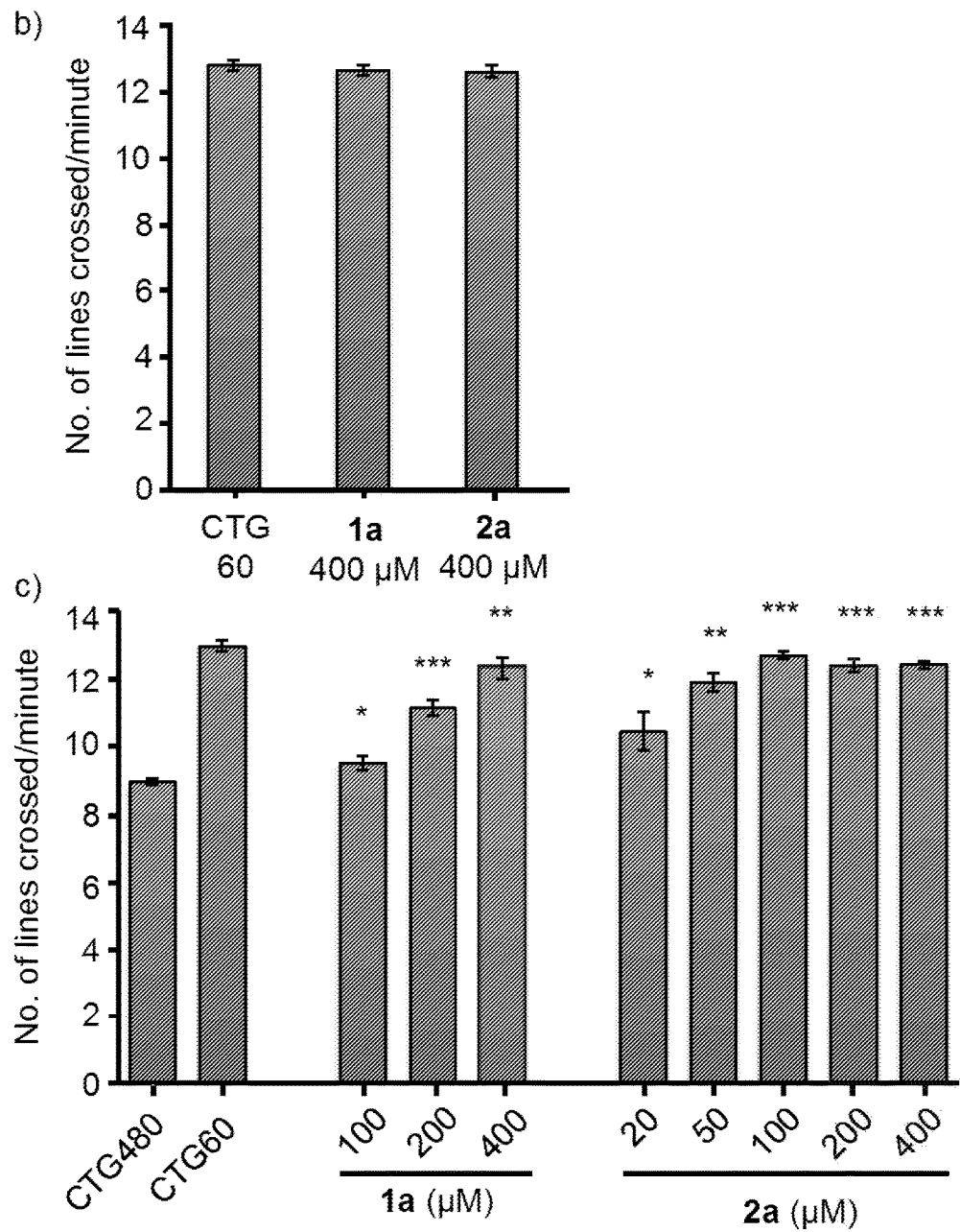
Fig. 4B-C

BISAMIDINIUM-BASED INHIBITORS FOR THE TREATMENT OF MYOTONIC DYSTROPHY

RELATED APPLICATIONS

This application is a National Stage filing under 35 U.S.C. § 371 of International Application No. PCT/US2015/044526, filed Aug. 10, 2015, which claims priority under 35 U.S.C. § 119(e) to U.S. Provisional Patent Application No. 62/034,932 filed Aug. 8, 2014, which applications are incorporated herein by reference.

GOVERNMENT SUPPORT

This invention was made with government support under Grant No. R01AR058361 awarded by the National Institutes of Health. The government has certain rights in the invention.

BACKGROUND OF THE INVENTION

Myotonic dystrophy type 1 (DM1) is an autosomal dominant neuromuscular disorder characterized by a range of symptoms that include muscle weakness (myopathy), difficulty relaxing muscles (myotonia), progressive muscle wasting (atrophy), cataracts, cardiac defect, and insulin dependent diabetes, There is an urgent need to discover lead agents for treating DM1 because it affects about 1 in 8,000 people, yet it remains incurable with no direct therapeutic options.

DM1 results from a progressive expansion of the trinucleotide CTG repeat in the 3'-untranslated region of the dystrophia myotonia protein kinase (DMPK) gene on chromosome 19q13.3. The number of CTG repeats is less than 35 in healthy people, and ranges from 50 to thousands in DM1 patients. The molecular origin of DM1 was previously attributed to three possible mechanisms: (1) DMPK haloinsufficiency, (2) decreased expression of neighboring genes, including SIX5 and DMAHP, and (3) a gain-of-function for the expanded RNA transcript ($rCUG^{exp}$). Recent studies have argued against the first two hypotheses, leaving the third mechanism as the favored one for therapeutic intervention.

The gain-of-function model involves expanded rCUG repeats forming stable stem-loop structures with U-U mismatches flanked by G-C and C-G base pairs, and sequestering important proteins. Key among these proteins is the muscleblind-like (MBNL) protein, a key alternative splicing regulator. The loss of MBNL1 results in abnormal alternative splicing of more than 100 pre-mRNAs, including cardiac troponin T (cTNT), insulin receptor (IR) and chloride channel 1 (CIC-1). Supporting the toxic RNA model is the finding that overexpression of MBNL1 protein in the skeletal muscle of a DM1 mouse model relieved the myotonia and abnormal RNA splicing. The MBNL1-$rCUG^{exp}$ complex formation has emerged as a key therapeutic target for DM1. Because there are currently no effective therapies for DM1, there is an urgent need for a new compounds and methods for the study and treatment of the disease.

SUMMARY

The invention provides disamidinium-based inhibitors that can be used as therapeutic agents, for example, for the treatment of myotonic dystrophy type 1 (DM1). The invention also provides potent inhibitors of protein sequestration by expanded triplet (CUG) repeats. Administration of the inhibitors show phenotypic improvement in a *Drosophilia* model of myotonic dystrophy.

The invention provides a compound of Formula I:

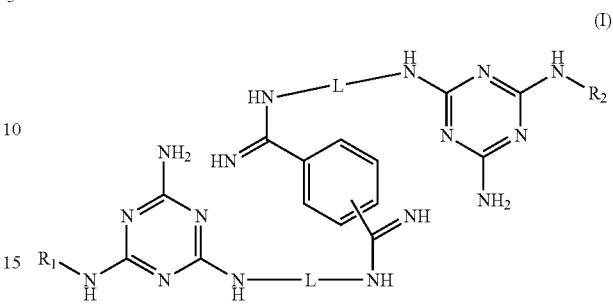

(I)

wherein
 $R^1$ is H, —($C_1$-$C_8$)alkyl-C≡CH, or —($C_1$-$C_8$)alkyl-$N_3$;
 $R^2$ is H, —($C_1$-$C_8$)alkyl-C≡CH, —($C_1$-$C_8$)alkyl-$N_3$, or a moiety of Formula 1A:

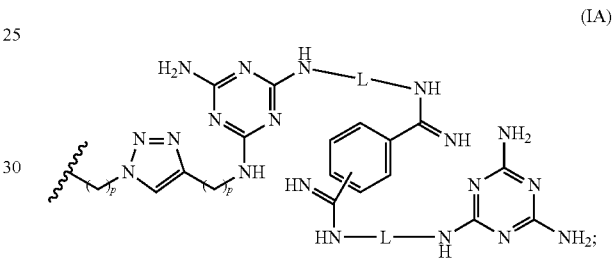

(IA)

wherein
 each p is independently 1-8; and
 each L is independently —($C_3$-$C_5$)alkylene-, —($C_2$-$C_5$) alkylene-interrupted by one oxygen, 1,3-cyclopenylene, 1,3-cyclohexylene, or 1,4-cyclohexylene;
 provided that one of $R^1$ and $R^2$ is not H; or a salt or solvate thereof;

In one embodiment, $R^1$ is —($C_1$-$C_8$)alkyl-C≡CH, such as $C_1$-alkyl-C≡CH, $C_2$-alkyl-C≡CH, $C_3$-alkyl-C≡CH, $C_4$-alkyl-C≡CH, $C_5$-alkyl-C≡CH, $C_6$-alkyl-C≡CH, $C_7$-alkyl-C≡CH, or $C_8$-alkyl-C≡CH. In another embodiment, $R^1$ is —($C_1$-$C_8$)alkyl-$N_3$, such as $C_1$-alkyl-$N_3$, $C_2$-alkyl-$N_3$, $C_3$-alkyl-$N_3$, $C_4$-alkyl-$N_3$, $C_5$-alkyl-$N_3$, $C_6$-alkyl-$N_3$, $C_7$-alkyl-$N_3$, or $C_8$-alkyl-$N_3$.

In one embodiment, $R^2$ is —($C_1$-$C_8$)alkyl-C≡CH, such as $C_1$-alkyl-C≡CH, $C_2$-alkyl-C≡CH, $C_3$-alkyl-C≡CH, $C_4$-alkyl-C≡CH, $C_5$-alkyl-C≡CH, $C_6$-alkyl-C≡CH, $C_7$-alkyl-C≡CH, or $C_8$-alkyl-C≡CH. In another embodiment, $R^2$ is —($C_1$-$C_8$)alkyl-$N_3$, such as $C_1$-alkyl-$N_3$, $C_2$-alkyl-$N_3$, $C_3$-alkyl-$N_3$, $C_4$-alkyl-$N_3$, $C_5$-alkyl-$N_3$, $C_6$-alkyl-$N_3$, $C_7$-alkyl-$N_3$, or $C_8$-alkyl-$N_3$.

A specific value for $R^1$ is H. Another specific value for $R^1$ is propargyl (—$CH_2$—C≡CH). Another specific value for $R^1$ is -ethyl-C≡CH (—$CH_2CH_2$—C≡CH). Another specific value for $R^1$ is -propyl-C≡CH (—$CH_2CH_2CH_2$—C≡CH). Another specific value for $R^1$ is -ethyl-$N_3$(—$CH_2CH_2$—$N_3$). Another specific value for $R^1$ is -propyl-$N_3$(—$CH_2CH_2CH_2$—$N_3$). Another specific value for $R^1$ is -butyl-$N_3$(—$CH_2CH_2CH_2CH_2$—$N_3$).

A specific value for $R^2$ is H. Another specific value for $R^2$ is propargyl. Another specific value for $R^2$ is -ethyl-C≡CH. Another specific value for $R^2$ is -propyl-C≡CH. Another specific value for $R^2$ is -ethyl-$N_3$. Another specific value for $R^2$ is -propyl-$N_3$. Another specific value for $R^2$ is -butyl-$N_3$.

In one embodiment, $R^1$ is H, propargyl, -ethyl-C≡CH, -propyl-C≡CH, -ethyl-$N_3$, -propyl-$N_3$, or -butyl-$N_3$. In some embodiments, $R^2$ is H, propargyl, -ethyl-C≡CH, -propyl-C≡CH, -ethyl-$N_3$, -propyl-$N_3$, or -butyl-$N_3$.

In one specific embodiment, $R^1$ is H and $R^2$ is propargyl or —$CH_2CH_2$—C≡CH. In another specific embodiment, $R^1$ is H an $R^2$ is —($C_2$-$C_4$)alkyl-$N_3$. In other embodiments, $R^1$ and $R^2$, independently of one another, are each either propargyl or —$CH_2CH_2$—C≡CH. In various embodiments, $R^1$ and $R^2$ are each —($C_2$-$C_4$)alkyl-$N_3$.

In another embodiment, $R^2$ is a moiety of Formula IA. Specific examples include embodiments where $R^2$ is the moiety of Formula IA and $R^1$ is H, where each p is independently 1, 2, or 3, and each L of the moiety of Formula IA is, independently of one another, propylene, butylene, or pentylene, or any combination thereof.

The substituents on the central phenyl ring of Formula I can be in an ortho, meta, or para orientation with respect to each other. In certain specific embodiments, the substituents on the central phenyl ring of Formula I are in a para orientation. Similar variability applies to the substituents on the central phenyl ring of the moiety of Formula IA. Accordingly, in various embodiments, the compound of Formula I can be a compound of Formula I-2:

(I-2)

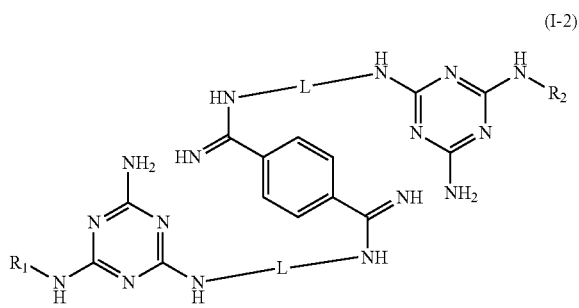

wherein each variable is as defined for the moiety of Formula IA.

The variables L can be characterized as linker groups. In any embodiment described herein, the variables L can be the same or different from each other. Examples of when L is a —($C_2$-$C_5$)alkylene- interrupted by one oxygen include —$CH_2OCH_2$—, —$CH_2OCH_2CH_2$—, —$CH_2CH_2OCH_2$—, —$CH_2OCH_2CH_2CH_2$—, —$CH_2CH_2CH_2OCH_2$—, —$CH_2CH_2OCH_2CH_2$—, —$CH_2OCH_2CH_2CH_2CH_2$, —$CH_2CH_2OCH_2CH_2CH_2$—, and the like. Several embodiments include compounds where each L is independently propylene, butylene, or pentylene. Accordingly, a compound of Formula I or I-2 can be a compound of Formula II:

(II)

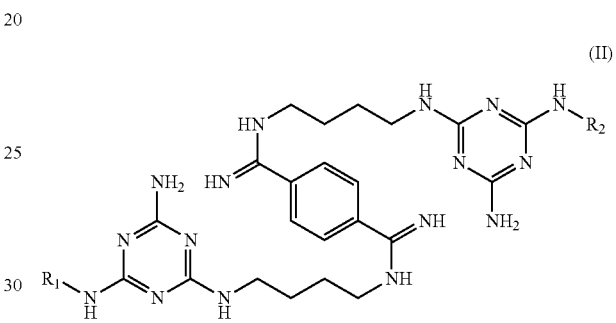

wherein each variable is as defined for Formula I. In certain embodiments, $R^1$ is H and $R^2$ is propargyl, —$CH_2CH_2$—C≡CH, or propyl-$N_3$.

In one specific embodiment, the compound of Formula I can be:

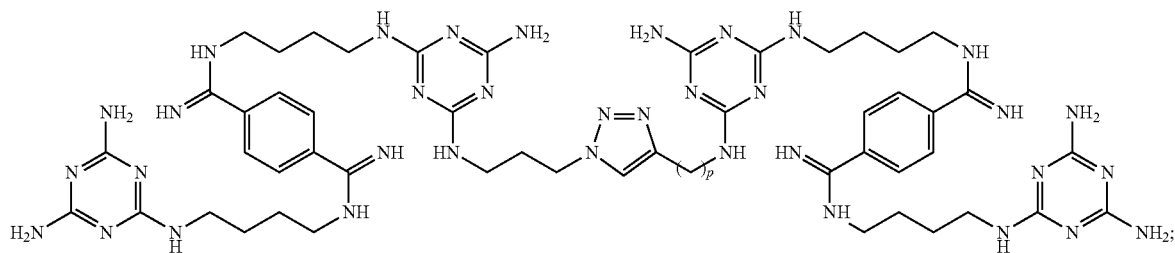

wherein each variable is as defined for Formula I. Furthermore, compounds of Formula I and I-2 can include moieties of Formula IA-2:

(IA-2)

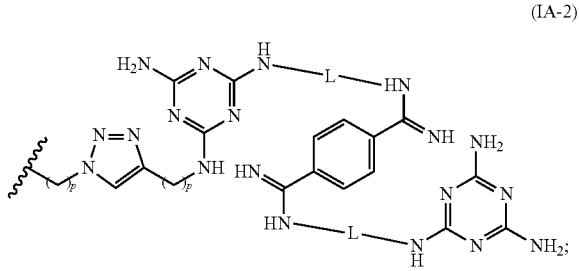

wherein p is 1 or 2; or a salt or solvate thereof.

Compounds of Formula I are typically prepared and/or isolated as salts, such as their tetra, octa, or nona HCl salts. The compounds can also be prepared and isolated as a variety of other salts or solvates, such as a salt described herein below, and as would be readily recognized by one of skill in the art.

The invention also provides a pharmaceutical composition comprising a compound of Formula I, or a sub-Formula thereof, in combination with a pharmaceutically acceptable diluent, carrier, or excipient.

The invention further provides a method of reducing the symptoms of myotonic dystrophy. The method can include administering to a patient having myotonic dystrophy an effective amount of a compound of Formula I, thereby reducing the symptoms of the myotonic dystrophy. The myotonic dystrophy can be myotonic dystrophy type 1 (DM1). The symptoms reduced by the administration can be, for example, one or more of muscle weakness (myopathy), difficulty relaxing muscles (myotonia), progressive muscle wasting (atrophy), cataracts, cardiac defect, and insulin dependent diabetes.

The invention thus provides novel compounds as described herein, intermediates for the synthesis of the compounds, as well as methods of preparing the compounds. The invention also provides compounds that are useful as intermediates for the synthesis of other useful compounds. The invention further provides for the use of compounds and compounds of the formulas described herein for the manufacture of medicaments useful for the treatment of diseases in a mammal, such as a human. Thus, the invention provides for the use of the compounds and compositions described herein for use in medical therapy, such as the treatment of myotonic dystrophy. The compositions can include a pharmaceutically acceptable diluent, excipient, or carrier.

BRIEF DESCRIPTION OF THE DRAWINGS

The following drawings form part of the specification and are included to further demonstrate certain embodiments of various aspects of the invention. In some instances, embodiments of the invention can be best understood by referring to the accompanying drawings in combination with the detailed description presented herein. The description and accompanying drawings may highlight a specific example, or a certain aspect of the invention. However, on skilled in the art will understand that portions of the example or aspect may be used in combination with other examples or aspects of the invention.

FIG. 1A-B. Determination of inhibition constants, $K_I$, by EMSA. (a) Representative gels showing the release of $(CUG)_{16}$ at different ligand concentrations. Top band is the MBNL1-$(CUG)_{16}$ complex, the bottom band is the free $(CUG)_{16}$. (b) $IC_{50}$ values were obtained by plotting the RNA fraction bound versus ligand concentrations. The apparent inhibition constant ($K_I$) was calculated using the equation: $K_I = IC_{50} \times K_D/[\text{protein}]_{total}$, where $K_D$ is the dissociation constant of the MBNL1-RNA complex and [protein] is at least 7-fold greater than the $K_D$. Error bars represent standard deviation of three independent experiments.

FIG. 2A-C. (a) Representative confocal microscope images showing the GFP-MBNL-rCUG$^{exp}$ foci disruption by compounds 1a and 2a. (b) Percent of foci area per cell after treatment of ligands for 48 h. The sequestration and dispersion of endogenous MBNL under the treatment of ligand are quantitatively measured. Error bars represent standard errors of mean from at least four independent experiments, two-tail t-test *P<0.005. Note: This was a head-to-head comparison between compounds 1a and 2a. In our previous study 100 µM 1a showed reduction of foci to 32%. The difference is attributed to variability in cells and conditions. (c) Cytotoxicity profile of compound 2a.

FIG. 3A-B. (a) Schematic representation of IR alternative splicing. (b) Correction of IR splicing by compounds 2a and 1a as determined by conventional RT-PCR. Error bars represent standard deviation for three independent experiments, two-tail t-test *P<0.01,**P<0.005.

FIG. 4A-C. Efficacy of 1a and 2a in DM1 Drosophilia fly mode. (a) Improvement in adult rough eye phenotype. Each experiment was conducted in triplicate. (b) Effect of ligands on the control Drosophilia larvae (24B–GAL4>UAS–(CTG)60). (c) Dose-dependent effect of ligands on the DM1 larvae (24B–GAL4>UAS–i(CTG)480). Each experiment was conducted in triplicate, 10 individual larvae for each trial. Error bars represent standard deviation, two tail t-test *P<0.05, P<0.01, *P<0.001.

DETAILED DESCRIPTION

Figure 2A:
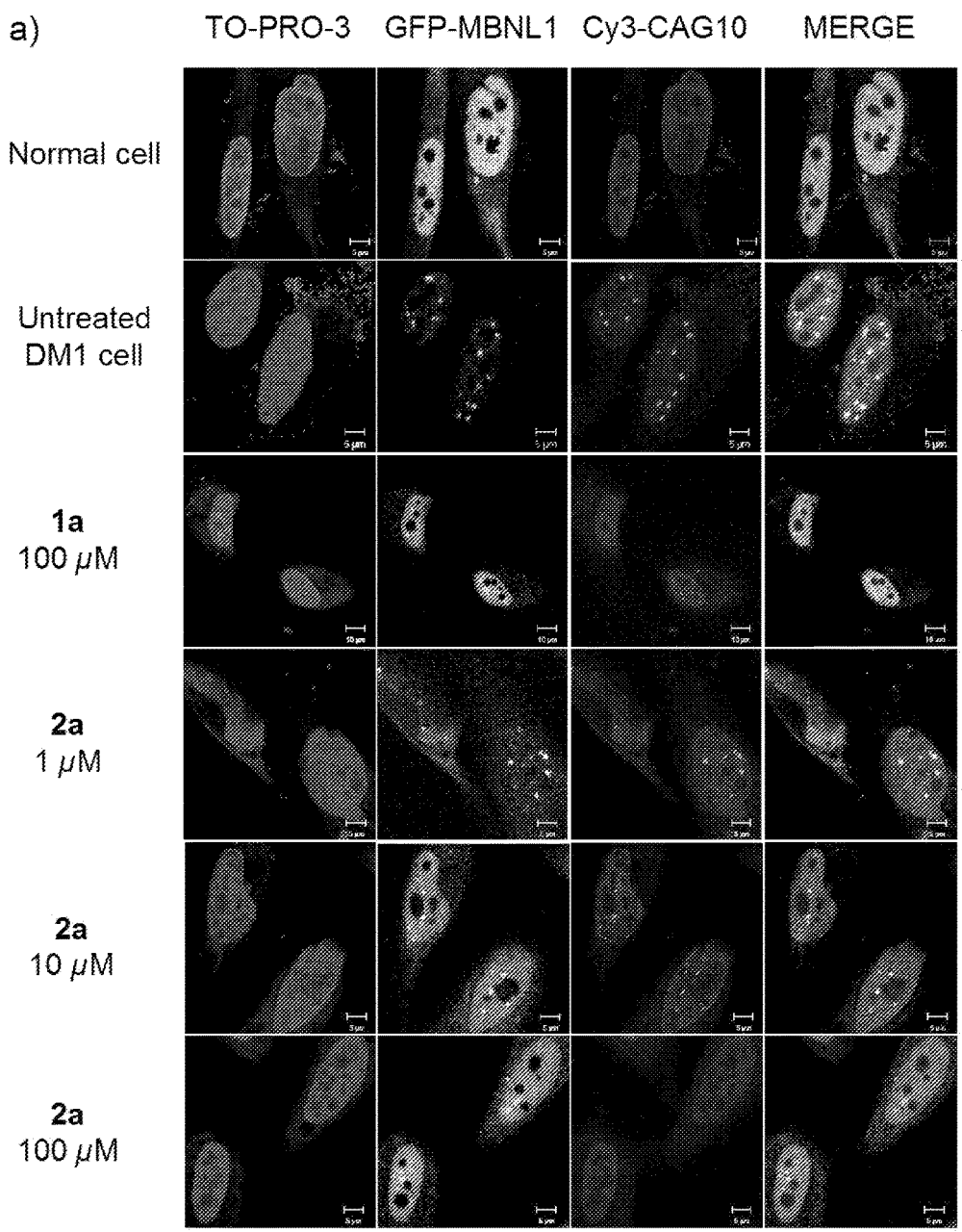

We have reported on the rational design of several acridine-containing ligands that strongly and selectively bind rCUG$^{exp}$ by intercalation (Arambula et al., Proc. Natl. Acad. Sci. U.S.A. 2009, 1006, 16068-16073; Jahromi et al., ACS Chem. Biol. 2013, 8, 1037-1043; Jahromi et al., J. Med. Chem. 2013, 56, 9471-9481). More recently, we discovered compound 1a, a second-generation ligand designed with two triaminotriazine recognition units linked to a bismidinium moiety, a known rCUG groove binder (Wong et al., J. Am. Chem. Soc. 2014, 136, 6355-6361).

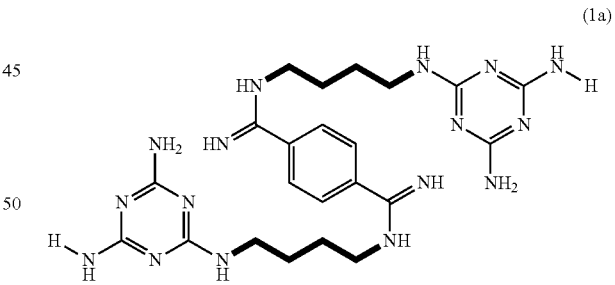

(1a)

Ligand 1a exhibited excellent water solubility and low cytotoxicity. Importantly, the compound both inhibited the formation of MBNL1-rCUG$^{exp}$ nuclear foci and dissolved foci that formed in DM1 model cells, thereby partially rescuing the mis-splicing of cTNT and IR pre-mRNA. However, compound 1a is only a weak inhibitor of the MBNL1-$(CUG)_{12}$ complex ($K_I$32 8=2 µM), so more effective agents were sought.

Previous work in our laboratory demonstrated that dimeric ligands can lead to enhancements in both the binding affinity and selectivity of rCUG-binding units. Herein we report the synthesis of compounds 1b-f, alkyne- and azide-containing analogs of compound 1a, that can be conveniently elaborated using the click reaction, which allows for a fragment-based drug discovery strategy. Initial interest in these compounds revolved around linking two units of 1a to create a bivalent ligand. We thus prepared bivalent compounds 2a and 2b. Dimer 2a is a more potent MBNL1-rCUG$^{exp}$ complex inhibitor than 1a, with favorable activity in DM1 model cells and a DM1 *Drosophilia* model.

structural data is still under development regarding the actual complex formed between 1a and rCUG$^{exp}$, both of these considerations suggest that a logical functionalization point would be the triaminotriazine amino group of 1a. Substituted analogs of dicyanobenzene and 1,4-diaminobutane are quite limited in availability and would require long

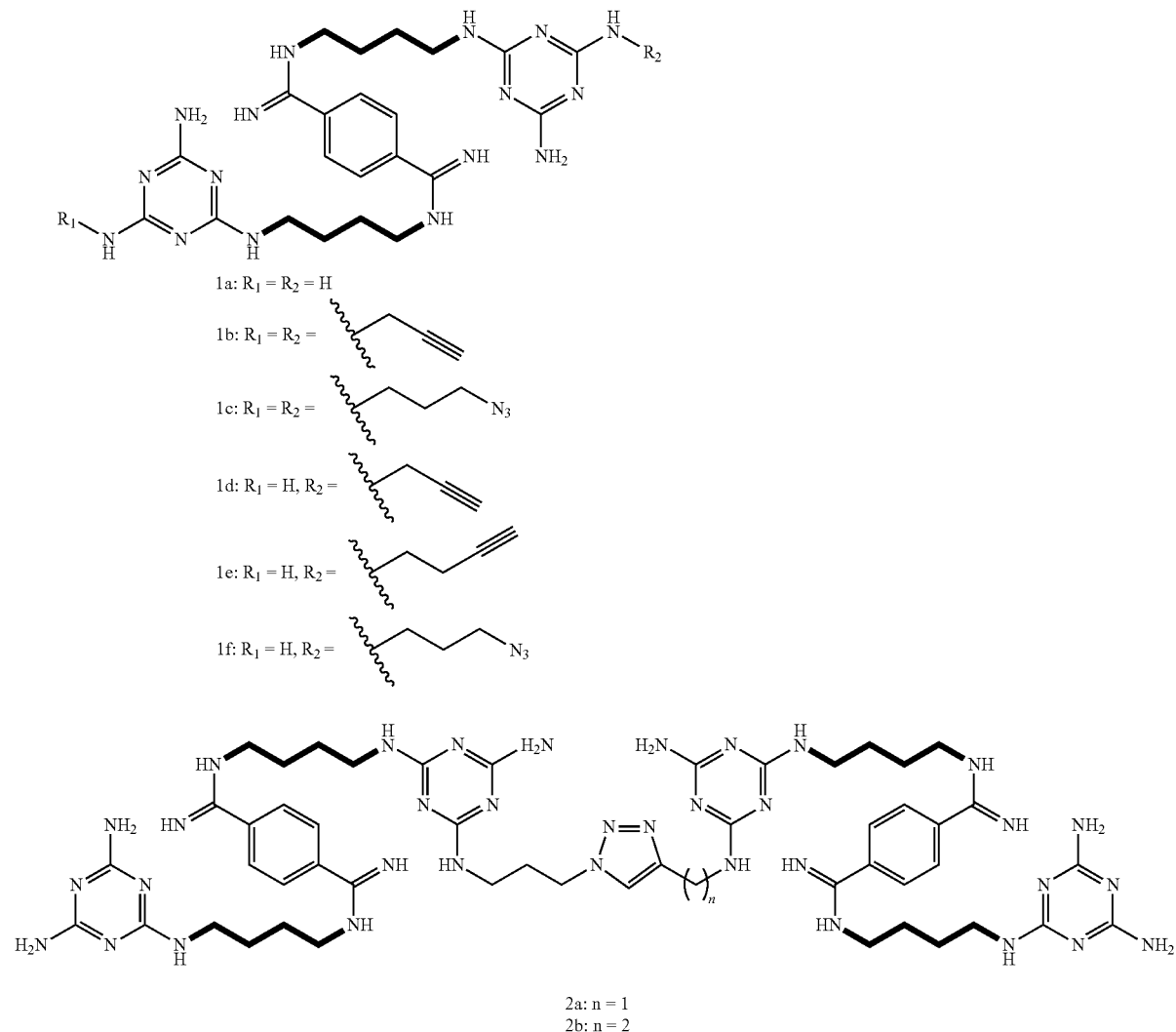

Design and Synthesis of Dimeric Ligands 2a-b.

The rational design of monomer 1a was based on a complex formed between a frame-shifting bisamidinium stimulator ligand and its HIV-1 frameshift site (FS) RNA stem-loop target. An overlay of the (CUG)$_{12}$ X-ray and the NMR-determined HIV-1 FS RNA structures showed striking similarities and the possibility of the bismidinium unit of 1a similarly binding the A-form CUG$^{exp}$ RNA major groove. Thus, the bisamidinium unit of 1a was designed to cover a central CUG with two triaminotrizine units recognizing the adjacent CUG sites.

There are a number of considerations in designing a dimeric ligand based on 1a. Two important considerations are synthetic accessibility and the ability to span adjacent binding sites without disrupting the primary interactions between the monomeric ligand and RNA. Although specific linker groups to span adjacent sites. In contrast, unsymmetrically substituted triaminotrazines are readily accessible synthetically.

We sought to determine if N-substitution of one or both of the triaminotriazine units of 1a would affect its ability to bind rCUG$^{exp}$. In a first generation series of rCUG$^{ex}$-targeting ligands containing acridine intercalculators, methylation of the amino groups in some cases had a profound effect on both affinity and selectivity. Thus, compounds 1b and 1c were designed to test the effect of N-substitution. Ligands 1b and 1c contain two small alkyne and azide moieties, respectively, the symmetric disubstitution making for a straightforward, three-step synthesis (Scheme 1A).

Scheme 1A. General synthesis of 1a-c.

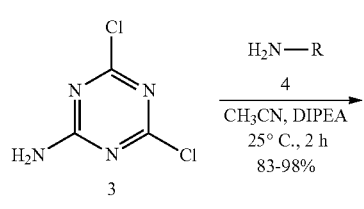

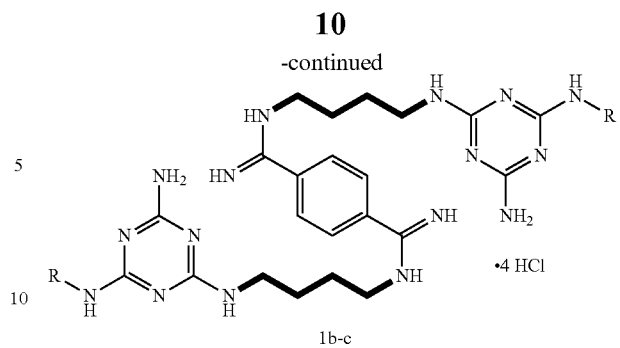

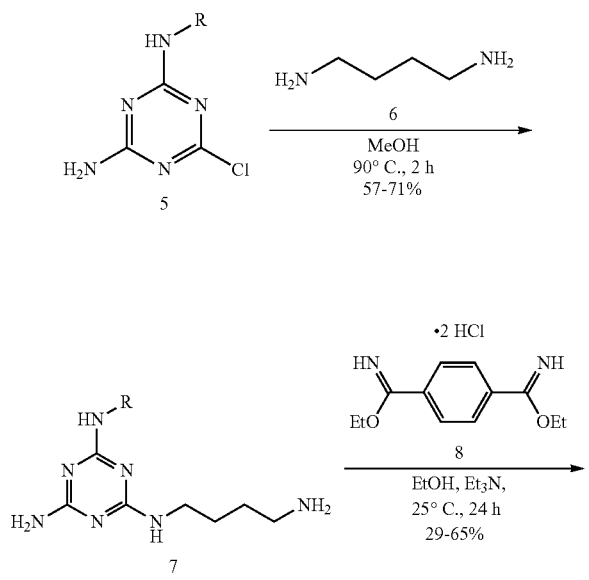

The alkyne and azide moieties were chosen because of their small size, excellent stability, and ultimate bioorthogonality. An isothermal titration calorimetry (ITC) experiment suggested that the binding affinity toward $(CUG)_{12}$ of compound 1b ($K_D$=7.7 µM) and 1c ($K_D$=4.8 µM) were comparable with that of compound 1a ($K_D$=8 µM) (FIG. 5). This finding enables the rapid development of a wide range of functional derivatives of ligand 1a using the [3+2] alkyne-azide cycloaddition ('click reaction') of 1b and 1c.

Synthesis of Dimeric Ligands Using Alkyne-Azide Cycloaddition.

Compounds 1d-f bearing one clickable group were prepared as described in Scheme 1B. Triaminotriazine 7 was readily prepared from the sequential substitutions of the 2-amino-4,6-dichloro-1,3,5 triazine 3 with amine 4 and 1,4-diaminobutane 6. Triaminotriazine 9 reacted with a large quantity of 8, which was obtained from the Pinner reaction of 1,4-dicyanobenzene with hydrochloric acid in anhydrous ethanol, to give 10 and a small amount of 1a. The mixture was treated with the appropriate 7 to give compounds 1d-f in moderate yields. Because hydrochloric acid was used in the purification, each compound 1 was a tetrahyrochloride salt.

Scheme 1B. General synthesis of 1d-f.

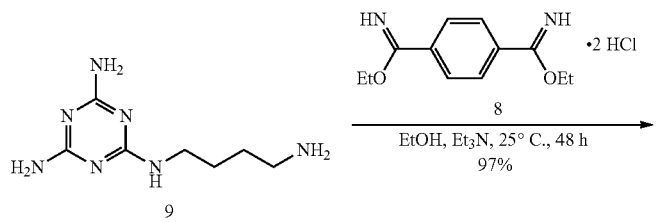

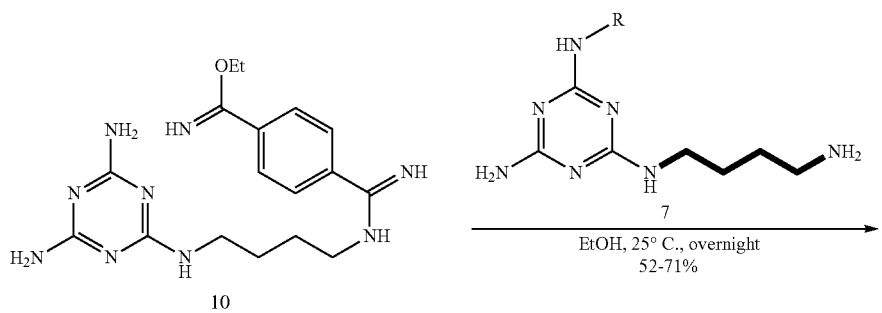

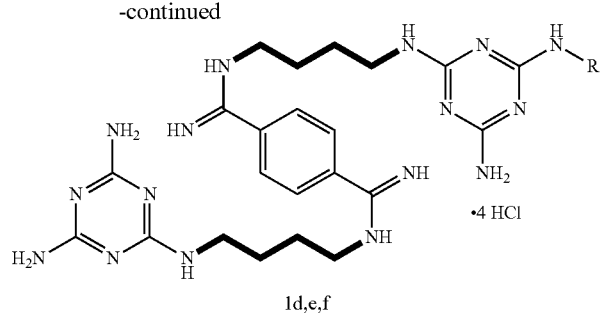

1d,e,f

Dimeric ligands 2a-d were prepared from the click reaction of 1d-e and 1f (Scheme 2). The azide-alkyne cycloadditions of 1d-e and 1f were assisted by in situ formation of copper (I) from the reduction of copper (II) sulfate by sodium ascorbate (see Meldal et al., *Chem. Rev.* 2008, 108, 2952-3015). The reactions were run in the presence of tris[(1-benzyl-1H-1,2,3-triazol-4-yl)methyl]amine (TBTA) to protect Cu(I) from oxidizing to Cu(II). Dimers 2a and 2b were purified by Sephadex CM-25 column and isolated as their hydrochloride salts. The desired compounds were judged to be 100% (2a) and 96% (2b) pure by analytical HPLC.

Inhibition of the MBNL1-$(CUG)_{16}$ Complex by Dimeric Ligands.

An electrophoretic mobility shift assay (EMSA) was employed to determine the in vitro inhibition of MBNL1-$rCUG^{exp}$ complex by monomer 1a and dimers 2a-b (FIG. 1). This study used $(CUG)_{16}$, which can form a hairpin structure containing a maximum of 8 U-U mismatches. Monomer 1a was designed to span 3 UU mismatches suggesting that the $(CUG)_{16}$ target provides at least one binding site for dimers 2a and 2b. Likely, a 1:1 complex was formed. In this study, a truncated MBNL1 (1-272 amino acids) containing four zinc finger motifs of MBNL1 and a hexahistidine tag Scheme 2. Synthesis of dimers 2a-b

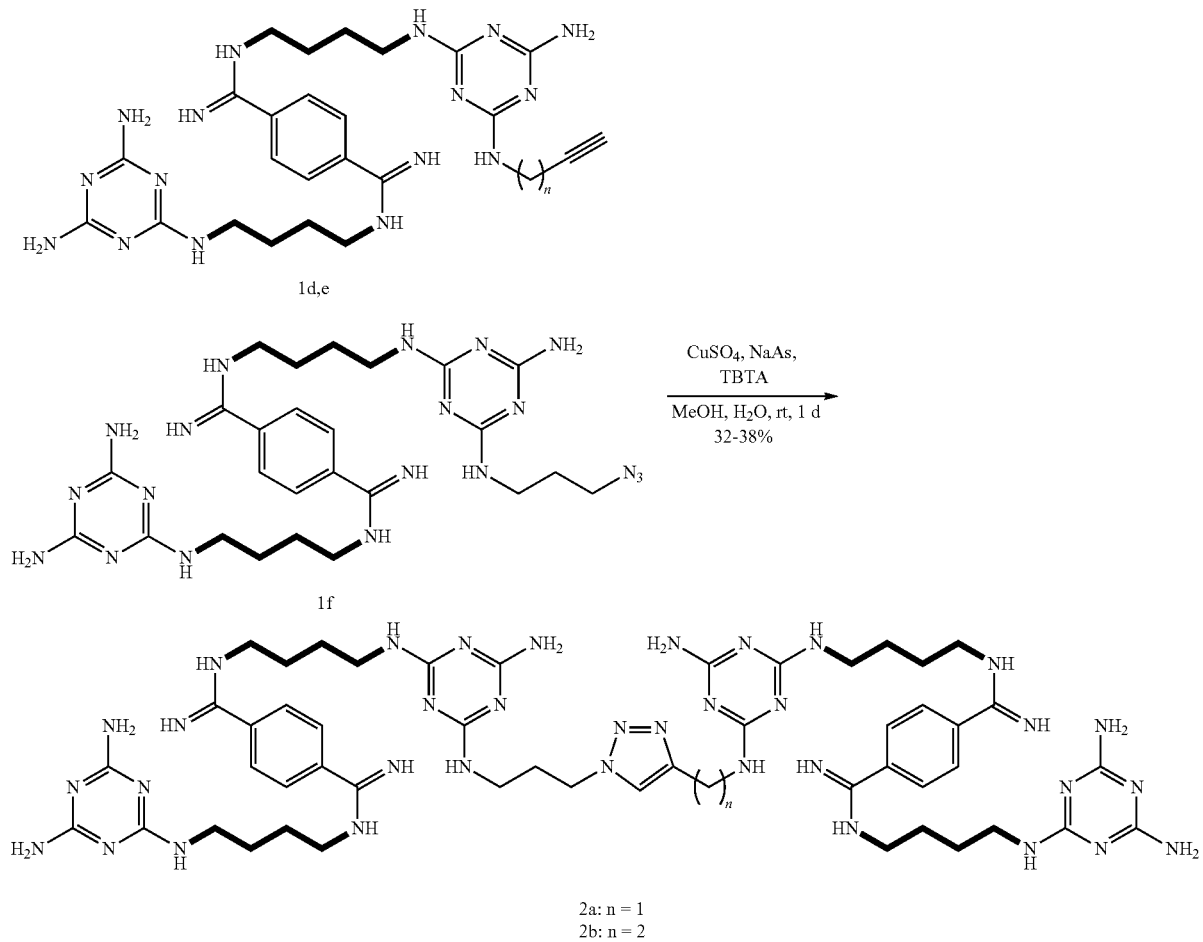

2a: n = 1
2b: n = 2

(C-terminus) was employed. This MBNL1 construct and the full-length MBNL1 have the similar affinities to rCUG repeats.

From the EMSA binding study, an apparent $K_D$ value of 5.1±1.6 nM was determined for the MBNL1 complex to radiolabeled-$(CUG)_{16}$ (FIGS. 6 and 7), which is consistent with reported $K_D$ value by EMSA and other techniques. To determine the inhibition constant of bivalent ligands 2a and 2b, the MBNL1-$(CUG)_{16}$ mixture, in which ca. 50% of the RNA is free, was incubated with various concentrations of ligand (FIG. 1a). The dimer concentrations were not raised to higher than 10 µM due to the aggregation on the gel at high concentrations. As the concentration of ligand increased, more RNA was released from the complex with MBNL protein. By fitting the plot of bound RNA fractions versus ligand concentrations with an appropriate equation, the $IC_{50}$ value was determined (FIG. 1b).

Dimer 2a exhibited and $IC_{50}$ value of 0.29±0.03 µM, and $K_I$=25±8 nM. Similarly, compound 2b gave an inhibition constant $K_I$=36±12 nM. In comparison, inhibition of MBNL1-$(CUG)_{16}$ complex by monomeric compound 1a was also determined by EMSA under identical conditions, which gave an $IC_{50}$ value of 189±33 µM, and a $K_I$ value of 16000±6000 nM, which is almost 1000-fold higher than that for 2a and 2b. The significant improvement in inhibition potency likely results from bivalent binding of $(CUG)_{16}$ by the dimeric ligands. We previously showed that the first generation acridine-based ligands and MBNL1 can form a ternary complex with rCUG repeat, indicating that inhibition may be noncompetitive. Whether compounds 2a and 2b sterically block MBNL1 binding or operate by a noncompetitive mechanism is currently not known, but beyond their greater RNA affinity, these ligands cover a greater surface areas of the rCUG$^{exp}$ target than monomer 1a.

Ligand 2a was selected for cellular and animal assays for two main reasons. First, it exhibited a slightly lower $K_I$ value than ligand 2b, although both values were within the experimental error of one another. More important was the lower cost and ready availability of propargylamine compared to 1-amino-3-butyne. This lower cost makes it easier to scale up the synthesis and prepare large quantities of 2a.

Ligand 2a Dissolved the MBNL1-$(CUG)_{16}$ Nuclear Foci in a DM1 Cell Model.

To evaluate the ability of dimer 2a to disrupt the MBNL1-$(CUG)_{16}$ foci in DM1 model cells, a standard fluorescence in situ hybridization experiment using exogenous MBNL was performed (FIG. 2a) (see Jahromi et al., ACS Chem. Biol. 2013, 8, 1037-1043). Here, GFP-MBNL1 was employed because of its intense signal and ability to easily monitor the location of the MBNL1 in live cells. Thus, normal HeLa cells were transfected with a plasmid containing GFP-MBNL1. To generate DM1 model cells, these HeLa cells were also transfected with a DMPK plasmid containing $(CTG)_{960}$. The nucleus was visualized by TO-PRO-3 as a blue area (Column 1). The presence of MBNL1 was indicated as a green color from GFP signal for GFP-MBNL1 (Column 2), whereas $(CUG)_{960}$ was detected by a complementary sequence $(CAG)_{10}$ conjugated with a Cy3 dye and represented by a red color (Column 3).

In normal cells, MBNL1 was observed throughout the nucleus, whereas in the DM1 model cells, it was concentrated in bright green spots that colocalized with red spots of $(CUG)_{960}$. The yellow spots in the merge (far right) column of FIG. 2a are nuclear foci. As can be seen, the foci dispersion was observed in the treatment of 1a at 100 µM or 2a at 1, 10, and 100 µM.

In addition, a parallel experiment using endogenous MBNL1 in place of GFP-MBNL1 was conducted to quantify foci reduction in a model that more closely resembles DM1 patient cells. The endogenous MBNL1 was detected by an immunofluorescence technique (Alexa Fluor® 488 dye-labeled antibody) (Wong et al., J. Am. Chem. Soc. 2014, 136, 6355-6361). It was found that approximately 72% of the nuclear foci remained after treatment with 1 µM of 2a for 48 h, whereas treatment of 1a at 100 µM reduced the number of foci to an even lesser extent (ca. 90%, FIG. 2a-b). However, dimer 2a did not exhibit a clear close-dependent effect (FIG. 2b). Incubation of 2a at 10 µM decreased the foci area to ca. 36%, but a similar level was also observed for the 100 µM treatment. It is encouraging that dimeric ligand 2a is as active at 1 µM as monomeric ligand 1a is at 100 µM. However, the lack of an obvious dose dependence and failure to fully dissolved nuclear foci at 100 µM may indicate a cellular penetration issue for 2a. Further study is underway.

Ligand 2a has a Low Cytotoxicity to HeLa Cells.

Although ca. 10% HeLa cell death was observed after the treatment of 2a at 100 µM for 96 h, the dimer showed negligible cellular toxicity at lower concentrations in a SRB assay (FIG. 2c). In contrast a dimeric series of acridine-based ligands was found to be quite cytotoxic. This finding indicates an advantage of the bisamidinium-based ligands over the acridine-containing ligands.

Ligand 2a Partially Corrects the IR Splicing.

Various studies have demonstrated the abnormal alternative splicing of pre-mRNAs that are directly associated with disease phenotypes in DM1 transgenic mouse models and DM1 patients. For example, mis-splicing of human cardiac troponin T (cTNT), insulin receptor (IR) in skeletal muscle tissue, and muscle-specific chloride channel (CIC-1) are correlated with, respectively, reduced myocardial function/conduction abnormalities, insulin resistance, and myotonia. In a mouse model, the overexpression of MBNL1 led to a correction of some of these splicing defects and reverse the disease phenotypes (e.g., myotonia and myopathy).

Because 2a is capable of inhibiting MBNL1-rCUG$^{exp}$ both in vitro and in cells, we evaluated its ability to correct the splicing defects in the DM1 cell model. We chose to examine the IR mRNA mis-splicing, because among several pre-mRNA splicing defects associated with the depletion of MBNL1 protein, the reversal of IR splicing requires the largest amount of free MBNL1 and is therefore the more challenging defect. During the alternative splicing of IR, two products were generated: isoforms IR-A and IR-B with the exclusion and inclusion of exon 11, respectively (FIG. 3a). In normal skeletal muscle, IR-B is the dominant isoform, whereas IR-A is more abundant in DM1 skeletal muscle. Consistent with previous studies, we found that normal HeLa cells and a DM1 cell model contained ca. 53% and 34% isoform B, respectively (FIG. 3b). Treatment of 2a in a DM1 cell model at different concentrations showed significant reversal of IR splicing. In particular, compound 2a at 1 µM increased the abundance of isoform B to 49% (ca. 80% correction). A similar effect was observed with the treatment of 2a at 10 and 100 µM or 1a at 100 µM.

Ligand 2a Suppresses the Disease Phenotypes in a DM1 Drosophila Model.

Determining drug efficacy in a living organism is a critical step in drug development. Drosophilia flies with tissue-specific expression of 480 interrupted CTG repeats, i(CTG)$_{480}$, show many key characteristics of DM1, such as nuclear accumulation of rCUG$^{exp}$ and MBNL proteins, CUG-induced eye phenotype, muscle degeneration, and abnormal alternative splicing of muscle genes. In contrast, Drosophila lines expressing 60 uninterrupted CTG repeats do not reproduce sever pathologies. Several small molecules have been reported to improve the CUG-induced phenotypes of DM1 Drosophila flies, including our previous studies of 1a. The comparative effectiveness of 1a and 2a in suppressing the rough eye phenotype and improving the larva's mobility were examined in the DM1 Drosophila model.

Figure 4A:
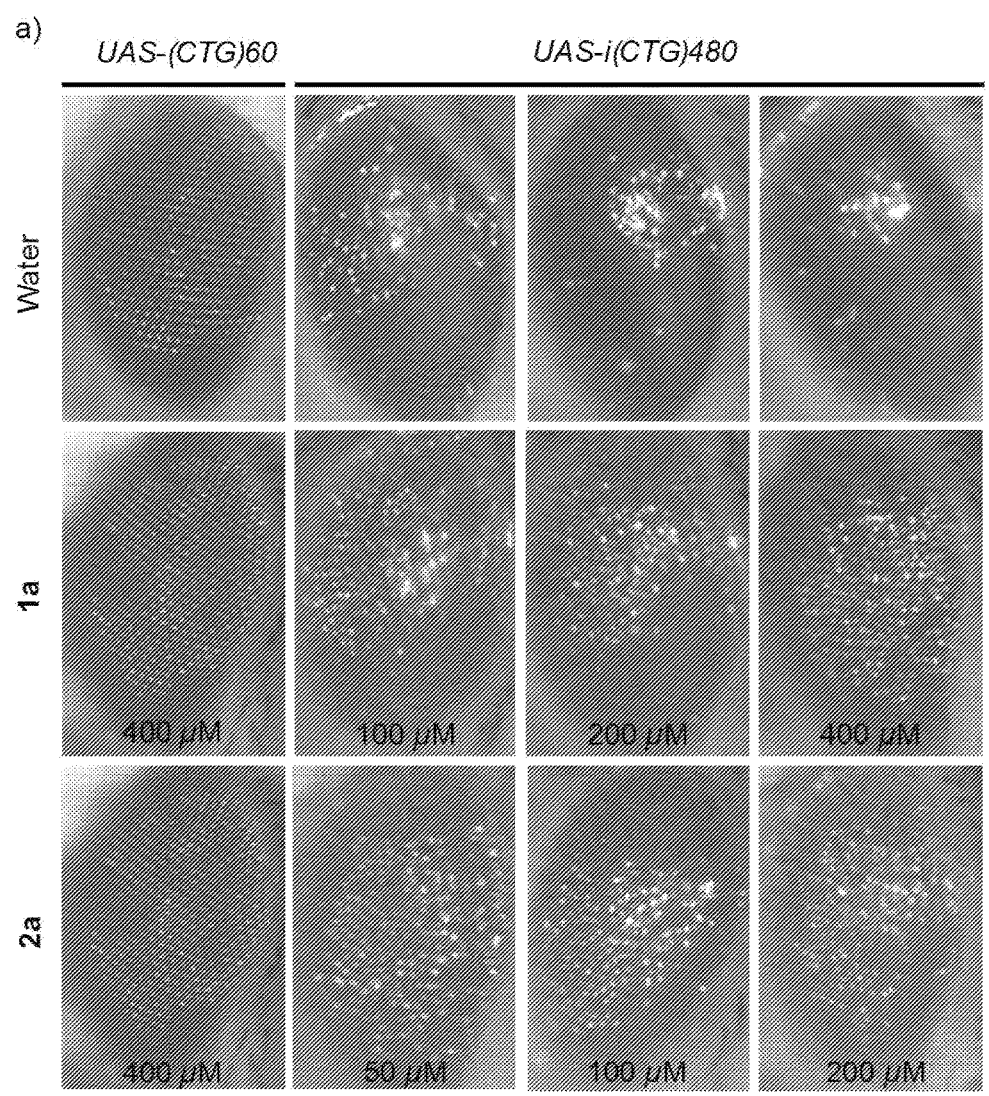

Similar to reported Drosophila models, our transgenic fly model with the gmr-GAL4 driven expression of i(CUG)$_{480}$ repeats (gmr-GAL4>UAS-i(CTG)$_{480}$) showed modified eye morphology, including disorganized ommatidia and mechanosensory bristles, resulting in a glossy eye (FIG. 4a). The microscope images showed that treatment with 50 μM of 2a led to a partial reversal of rough eye phenotypes, whereas the same effect was only achieved when the treatment with monomer 1a was raised to 400 μM (FIG. 4a). On the other hand, treatments of CTG60 Drosophila flies with either 1a or 2a at 400 μM did not change the fly's eye structure.

Recently, Jagla and coworkers demonstrated the mobility or locomotor defect of DM1 larvae using a contraction and righting assay (Picchio et al., Hum. Mol. Genet. 2013, 22, 2795-2810). We found that compounds 1a and 2a significantly improved the locomotor ability of DM1 Drosophila larvae using a larval crawling assay. An individual larva generated from transgenic flies was placed on a Petri dish over graph paper, and the number of grid lines crossed by the larva in 1 min was recorded. It was found that the healthy larvae are able to crawl ca. 13 lines per min, whereas the DM1 larvae can cross only 9 lines (FIG. 4c), demonstrating their locomotor defect. When the normal larvae are raised in the presences of 400 μM aqueous solution containing fly food of either 1a or 2a, the mobility is not affected (FIG. 4b), suggesting a low toxicity of the bisamidinium ligands.

Interestingly, treating DM1 larvae with 1a at 100, 200, and 400 μM demonstrated a dose response with ca. 14%, 54%, and 84%, respectively, of the crawling defect rescued, respectively. Compared to 1a, dimer 2a showed an even greater efficacy. The crawling movement was nearly full recovered at 100 μM of 2a. Even at concentrations as low as 20 μM, 2a induced a 37% improvement in the DM1 larva's mobility. To our knowledge, this is the first example of a small molecule showing a substantial improvement in locomotor behavior or muscle performance defect of the DM1 Drosophila larvae.

In summary, the high potency of the benzamidinium-based dimeric ligand 2a, prepared by a copper-catalyzed click reaction, was demonstrated by in vitro inhibition of the MBNL1-rCUG$^{exp}$ interaction, nuclear foci disruption in model DM1 cell culture, correction of IR mis-splicing defect, and a dose-dependent reversal of rCUG-induced phenotypes in a DM1 Drosophila model. Furthermore, compound 2a exhibited a ca. 1000-fold greater inhibitory power toward the MBNL1-rCUG$^{exp}$ interaction than compound 1a and promising effects in the DM1 Drosophila model.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14$^{th}$ Edition, by R. J. Lewis, John Wiley & Sons, New York, N.Y., 2001.

References in the specifications to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combinations of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one or four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identify within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecular are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups (groups from which a proton can be removed (e.g., —COOH) or added (e.g., amines) or which can be quaternized (e.g., amines)). All possible ionic forms of such molecules and salts thereof are indented to be included individually in the disclosure herein. With regards to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Whenever a range is given in the specification, for example, a temperature range, a time range, a carbon chain range, or a composition or concentration range, all intermediate ranges and subranges, as well as all individual values included in the ranges given are intended to be individually included in the disclosure. It will be understood that any subranges or individuals values in a range or subrange that are included in the description can be optionally excluded from embodiments of the invention.

Specific values listed below for radicals, substituents, and ranges, are for illustration only; they do not exclude other defined values or other values within defined ranges for the radicals and substituents. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decycl, dodecyl, and the like. The alkyl can be unsubstituted or substituted, for example, with a substituent described below. The alkyl can be a monovalent hydrocarbon radical, as described and exemplified above, or it can be a divalent hydrocarbon radical (i.e., an alkylene).

The alkyl groups of the various R groups, as well as the amino substituents of triazine rings and the central phenyl ring of the formula described herein may be substituted with one or more substituents. The term "substituted" indicates that one or more hydrogen atoms on the groups indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituents can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkythio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group. The substituents described above and throughout this specification can be applied to any synthetically available position of the various compounds described herein, including amine groups on the compounds described in U.S. Pat. No. 8,754,084 (Zimmerman et al.), which includes useful synthetic techniques and which is incorporated herein by reference. The linkers described in U.S. Pat. No. 8,754,084 (Zimmerman et al.) may also be used as the group L in Formula I and related formulas described herein.

The term "amino" refers to —$NH_2$, and the term "alkylamino" refers to —$NR_2$, wherein at least one R is alkyl and the second R is hydrogen, alkyl, a nitrogen protecting group or an optionally substituted substituent as described herein. The term "acylamino" refers to RC(=O)NH—, wherein R is as described previously.

The term "exposing" is intended to encompass the term as broadly understood in the art. In an embodiment, the term means to subject or allow to be subjected to an action, influence, or condition. For example and by way of example only, a cell can be subjected to the action, influence, or condition of a therapeutically effective amount of a pharmaceutically acceptable form of a therapeutic agent.

The term "contacting" refers to the act of touching, making contact, or of bringing to immediate or close proximity (i.e., exposing), including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. A "therapeutically effective amount" of a compound with respect to the subject method of treatment refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated, e.g., at a reasonable benefit/risk ratio applicable to any medical treatment.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. The term "treating" or "treatment" thus can include reversing, reducing, or arresting the symptoms, clinical signs, and underlying pathology of a condition in manner to improve or stabilize a subject's condition. However, when preventing is intended, it will be explicitly stated.

The terms "inhibit", "inhibiting", and "inhibition" refer to the slowing, halting, or reversing the growth or progression of a disease, infection, condition, or activity of a group of cells or an enzyme. The inhibition can be greater than about 20%, 40%, 60%, 80%, 90%, 95%, or 99%, for example, compared to the growth or progression that occurs in the absence of the treatment or contacting.

The phrase "maximum tolerated dose" is employed herein to refer to the highest dose of a pharmalogical treatment that will produce the desired effect without unacceptable toxicity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservative, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Generally Synthetic Methods

The invention also relates to methods of making the compounds and compositions of the invention. The compounds and compositions can be prepared by applicable techniques of organic synthesis. Many such techniques are well known in the art. For example, many techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol 5, Leroy G. Wade, Jr., 1984; and Vol. 6, Michael B. Smith; as well as standard organic reference texts such as *March's Advanced Organic Chemistry: Reactions, Mechanisms, and Structure*, 5th Ed. by M. B. Smith and J. March (John Wiley & Sons, New York, 2001), *Comprehensive Organic Synthesis: Selectivity, Strategy & Efficiency in Modern Organic Chemistry*, in 9 Volumes, Barry M. Trost, Ed.-in-Chief (Pergamon Press, New York, 1993 printing); *Advanced Organic Chemistry, Part B: Reactions and Synthesis*, Second Edition, Cary and Sundberg (1983); *Protecting Groups in Organic Synthesis*, Second Edition, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of compounds of the invention are provided below. These methods are intended to illustrate the nature of such preparations and are not intended to limit the scope of applicable methods. Generally, reaction conditions such as temperature, reaction time, solvents, work-up procedures, and the like, will be those common in the art for the particular reaction to be performed. The cited reference materials, together with the materials cited therein, contain detailed descriptions of such conditions. Typically the temperatures will be −100° C. to 200° C., solvents will be aprotic and protic, depending on the conditions required, and reaction times will be 1 minute to 2 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions the temperature is frequently reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are known in the art and can be applied when applicable.

Protecting Groups. The term "protecting group" refers to any group that, when bound to a hydroxyl, nitrogen, or other heteroatom, prevents undesired reactions from occurring at the sight of the heteroatom, and which group can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)), and any other group that can be introduced chemically onto a hydroxyl functionality and later selectively removed wither by chemical or enzymatic methods in mild conditions compatible with the nature of the product. The $R^1$ and $R^2$ groups of Formula I can also be protecting groups, as described herein.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (George Thieme Verlag Stuttgart, New York, 1994), which is incorporated herein by reference in its entirety. Some specific protecting groups that can be employed in conjunction with the methods of the invention are discussed below.

In general, modifications to the compounds and formulas described herein can be made according to organic synthesis techniques known to those of skill in the art and/or according to the synthetic schemes provided herein. Where desired, synthesis of a compound can begin with commercially available chemicals, from compounds described in the chemical literature, or from products of the reactions and methods described herein. Commercially available compounds may be obtained from standard commercial sources including Acros Organics (Pittsburgh, Pa.), Aldrich Chemical (Milwaukee Wis., including Sigma Chemical and Fluka), Aurora Fine Chemicals (San Diego, Calif.), Acorn Pharmatech (Redwood City, Calif.), Atomax Chemical Co. (Shenzhen, China), Eastman Organic Chemicals, Eastman Kodak Company (Rochester, N.Y.), Fisher Scientific Co. (Pittsburgh, Pa.), ICN Biomedicals, Inc. (Costa Mesa, Calif.), Lancaster Synthesis (Windham, N.H.), Spectrum Quality Product, Inc. (New Brunswick, N.J.), TCI America (Portland, Oreg.), Wako Chemical USA, Inc. (Richmond, Va.), and the like. Other starting materials and intermediates can be readily prepared in one to a few steps from commercially available starting materials using standard synthetic transformations familiar to those of skill in the art.

Salts and Solvates

The compounds described herein can be purified and isolated in their free-base or free-acid forms or they can be isolated in their salt forms, for example, hydrohalide salts, including salts with two, three, four or more equivalents of the hydrohalide, as appropriate.

Pharmaceutically acceptable salts of compounds described herein are within the scope of the invention and include acid or base addition salts which retain the desired pharmalogical activity and are not biologically undesirable (e.g., the salt is not unduly toxic, allergenic, or irritating, and is bioavailable). When a compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzesulfonic acid, naphthalene sulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free-base or free-acid form with a suitable acid or base, respectively, and isolating the salt thus formed.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds described herein, one of ordinary skill in the art can select from among a wide variety of available couterions those that are appropriate for preparation of salts of this invention for a given application. In specific applications, the selection of a given anion or cation for preparation of a salt may result in increased or decreased solubility of that salt.

Examples suitable salts of the compounds described herein include their hydrochlorides, hydrobromides, sulfates, methansulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art. Also included are base addition salts such as sodium, potassium, calcium, ammonium, organic amino, or magnesium salts, or a similar salt.

When compounds described herein contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as salts derived from organic acids like acetic, behenic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention can contain both basic and acidic functionalities that allow the compounds to be converted into either base or acid addition salts.

Certain compounds of the invention can exist in unsolvated forms as well as in solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix. The compounds of the formulas described herein can be hydrates.

Pharmaceutical Formulations

The following describes information relevant to pharmaceutical and pharmalogical embodiments and is further supplemented by information in the art available to one of ordinary skill. The exact formulation, route of administration and dosage can be chosen by an individual physician in view of a patient's condition (see e.g., Fingl et al., in *The Pharmalogical Basis of Therapeutics*, 1975, Ch. 1).

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

A compound may be combined with different types of carriers depending on whether it is to be administered in solid, liquid or aerosol form, and whether it needs to be sterile for certain routes of administration, such as an injection. Compounds and compositions described herein can be administered intravenously, intradermally, intraarterially, intraperitoneally, intralesionally, intracranially, intraarticulary, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, *Remington's Pharmaceutical Sciences*, 18th Ed. Mack Printing Company, 1990).

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring agent such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will be generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the use.

Examples of dermatological compositions for delivering active agents to the skin are known in the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known in the art; for example, see U.S. Pat. No. 4,938,949 (Borch et al.). The amount of a compound, or an active salt or derivative thereof, required for use in treatment will vary not only with the particular compound or salt selected, but also with the route of administration, the nature of the condition being treated, and the age and condition of the patient, and will be ultimately at the discretion of an attendant physician or clinician.

It should be noted that the attending physician would know how to and when to terminate, interrupt, or adjust administration due to toxicity, organ dysfunctions, etc. Conversely, the attending physician would also know to adjust treatment to higher levels if the clinical responses were not adequate (in light of or precluding toxicity aspects). The magnitude of an administered dose in management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g., the age, body weight, and response of an individual patient.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of a compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight, to about 100 mg/kg/body weight, etc., can be administered, based on the numbers described above.

In any case, the composition may comprise various antioxidants to retard oxidation of one or more component. Additionally, the prevention of the action of microorganisms can be brought about by preservative such as various antibacterial and antifungal agents, including, but not limited to parabens (e.g., methylparabens, propylparabens), chlorobutanol, phenol, sorbic acid, thimerosal, or combinations thereof.

The following Examples are intended to illustrate the above intention and should not be constructed as to narrow its scope. One skilled in the art will readily recognize that the Examples suggest many other ways in which the invention could be practiced. It should be understood that numerous variations and modifications may be made while remaining within the scope of the invention.

EXAMPLES

Abbreviations: DM1, myotonic dystrophy type 1; cTNT, cardiac troponin T; ClC-1; Chloride channel 1; IR, insulin receptor; DMAHP, DM-associated homeo domain protein; DMPK, dystrophia myotonia protein kinase; EMSA, electrophoretic mobility shift assay; FISH, fluorescence in situ hybridization; MBNL, musclebind-like; RT-PCR, reverse transcription polymerase chain reaction; TBTA, tris[(1-benzyl-1H-1,2,3-triazol-4-yl)methyl]amine; SBR, sulfo-rhodamine B.

Example 1. Compound Preparation

Synthetic Procedures.

Unless otherwise noted, $^1$H and $^{13}$C NMR spectra were recorded on a 500 MHz Varian Unity Inova spectrometer. All NMR measurements were carried out in either $CDCl_3$ or DMSO-$d_6$ at ambient temperature. Chemical shifts are in parts per million (ppm), relative to the residual peaks of $CDCl_3$ ($^1$H: 7.26; $^{13}$C: 77.16) or DMSO-$d_6$ ($^1$H: 2.50; $^{13}$C: 39.25). Coupling constants (J) were reported in Hertz. Electrospray ionization mass spectra (ESI-MS) was used for mass spectrometry analysis.

All non-aqueous reactions were carried out under a dry $N_2$ atmosphere with oven-dried (115° C.) glassware. All solvents and reagents were of reagent quality, purchased commercially, and used without further purification unless otherwise indicated. Anhydrous tetrahydrofuran (THF), dimethylformamide (DMF), and dichloromethane (DCM) were obtained from a solvent purification system (SPS).

Reactions were monitored by thin layer chromatography using EMD pre-coated silica gel 60 $F_{254}$ plates. Non-fluorescent compounds were visualized with a spray of 5% (w/v) phosphomolybdic acid hydrate in ethanol with subsequent heating. Flash chromatography was carried out using Silicycle Siliaflash® P60 (230-400 mesh) silica gel.

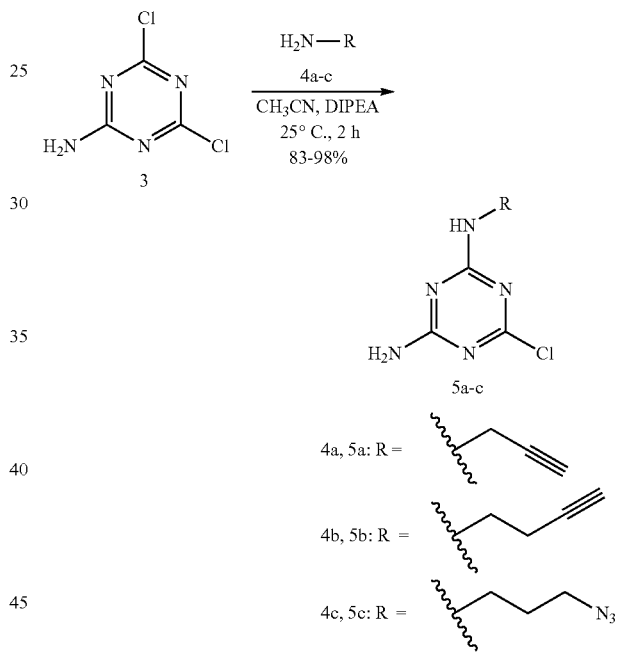

General Procedure for Preparation of Compounds 5a-c.

To a suspension of 14.0 g (84.9 mmol) of 2-amino-4,6-dichloro-1,2,3-triazine 3 and 15 mL (86.1 mmol) of DIPEA in 160 mL of $CH_3CN$ was added 5.0 g (90.8 mmol) of propargylamine 4a at room temperature. The mixture was stirred at room temperature for 2 h. The white solid was filtered, washed with DI water and dried under nitrogen overnight to give 13.0 g (83%) of product 5a as a white solid. $^1$H NMR: δ 8.12-7.94; (m, NH, 1H), 7.45-7.24; (m, $NH_2$, 2H), 4.01-3.98; (m, $CH_2$, 2H), 3.09; (t, J=2.5. CCH, 1H), $^{13}$C NMR: δ 168.28, 166.64, 165.35, 80.66, 72.18, 29.33. ESI-MS (m/z) calculated for [M+H]$^+$: 184.0; found 184.0; ([M+H]$^+$, 100%).

Using the general procedure described above, 0.6 g (3.6 mmol) of 3, 0.95 mL (5.5 mmol) of triethylamine, and 0.35 mL (4.3 mmol) of 4b afforded 0.7 g (98%) of 5b as a white solid. $^1$H NMR: δ 7.84-7.66; (m, NH, 1H), 7.35-7.14; (m, $NH_2$, 2H), 3.36-3.28; (m, $NHCH_2$, 2H), 2.84-2.82; (m, CCH, 1H), 2.39-2.33; (m, $CCH_2$, 2H).

Using the general procedure described above, 8.4 g (50.9 mmol) of 3, 7.5 mL (53.8 mmol) of triethylamine, and 6.0 g (59.9 mmol) of 3-azido-propylamine 4c afforded 9.8 g (84%) of 5c as a white solid. $^1$H NMR: δ 7.83-7.65; (m, NH, 1H), 7.33-7.10; (m, NH$_2$, 2H), 3.40-3.36; (m, NHCH$_2$, 2H), 3.28-3.23; (m, N$_2$CH$_2$, 2H), 1.75-1.68; (m, CH$_2$, 2H).

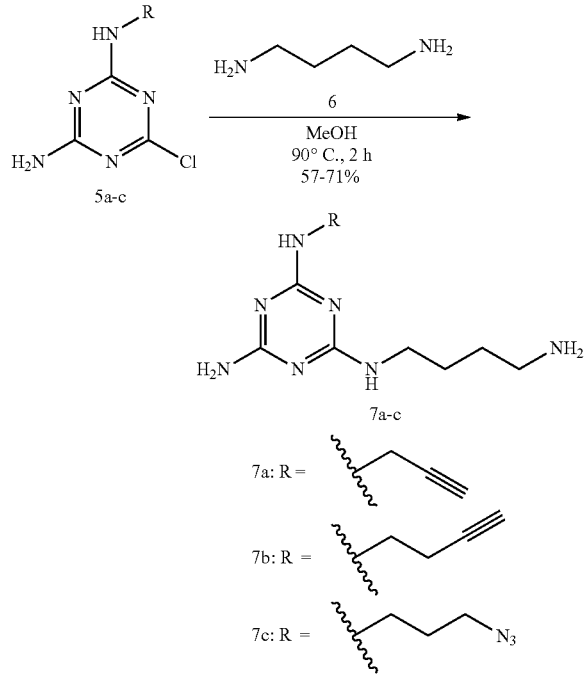

General Procedure for Preparation of Compounds 7a-c.

To a mixture of 22 mL (218.9 mmol) of diaminobutan 6 in 50 mL of methanol was added slowly 13.0 g (71.1 mmol) of 5a over 30 min at 90° C. The mixture was stirred at 90° C. for 1 h. The solvent and the excess amount of diaminobutane were removed by distillation. The resulting solid was purified by Silica gel column chromatography with a gradient mixture of CH$_2$Cl$_2$ and MeOH from 9:1 to 4:1. Fractions containing product were combined and concentrated using a rotary evaporator to give 11.9 g (71%) of 7a as a white solid. $^1$H NMR: δ 6.83-6.52; (m, NH, 2H), 6.26-5.98; (m, NH$_2$, 2H), 4.68; (br s, NH$_2$, 2H), 3.97-3.95; (m, CCH$_2$, 2H), 3.21-3.15; (m, NHCH$_2$, 2H), 3.00; (t, J=2.4, CCH, 1H), 2.62; (t, J=6.9, NH$_2$CH$_2$, 2H), 1.47-1.39; (m, CH$_2$CH$_2$, 4H). $^{13}$C NMR: δ 166.97, 166.73, 165.97, 165.77, 165.57, 82.72, 72.16, 41.31, 30.41, 29.22, 26.89. ESI-MS (m/z) calculated for [M+H]$^+$: 236.2; found 236.1.

Using the general procedure described above, 0.7 g (3.5 mmol) of 5b and 1.5 mL (14.9 mmol) of 6 afforded 0.5 g (57%) of 7b as a white solid. $^1$H NMR: δ 6.59-6.45; (m, NH, 2H), 6.22-5.75; (m, NH, 2H), 4.12; (br s, NH$_2$, 2H), 3.34-3.29; (m, NHCH$_2$, 4H), 2.81; (t, J=2.7, CCH, 1H), 2.66; (t, J=6.8, NH$_2$CH$_2$, 2H), 2.33; (br s, CCH$_2$, 2H), 1.45; (br s, CH$_2$, 4H).

Using the general procedure described above, 9.3 g (40.7 mmol) of 5c and 13 mL (129.3 mmol) of 6 afforded 7.5 g (66%) of 7c as a white solid. $^1$H NMR: δ 8.07; (br s, CH$_2$NH$_2$, 2H), 6.67-6.46; (m, NH, 2H), 6.17-5.89; (m, NH$_2$, 2H), 3.36; (t, J=6.8 NHCH$_2$, 2H), 3.23-3.15; (m, NHCH$_2$ and N$_3$CH$_2$, 4H), 2.74; (t, J=7.5, NH$_2$CH$_2$, 2H), 1.72-1.69; (m, CH$_2$, 2H), 1.59-1.46; (m, CH$_2$CH$_2$, 4H). ESI-MS (m/z) calculated for [M+H]$^+$: 281.12; found 281.1.

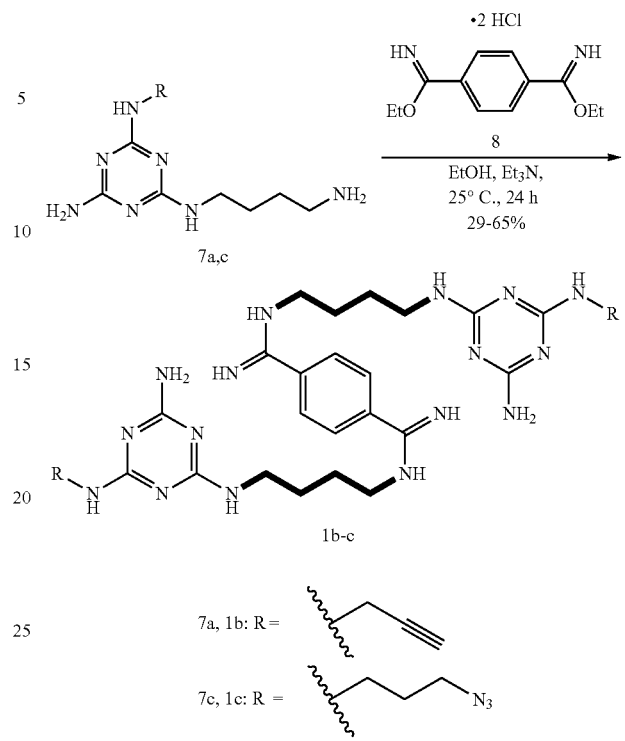

General Procedure for Preparation of Compounds 1b-c.

To a white suspension of 1.5 g (5.1 mmol) of 8 in 30 mL of anhydrous EtOH was added 3.3 mL (23.7 mmol) of anhydrous Et$_3$N. To the resulting clear solution was added 13 mL (13.0 mmol) of 1M ethanolic solution of 7a. The reaction mixture was stirred at room temperature for 24 h. The solvent was removed using a rotary evaporator. The white solid was purified by silica gel column chromatography with a gradient mixture of CH$_2$Cl$_2$ and MeOH from 9:1 to 1:9 (v/v). After using 1 L of DCM/MeOH (1:9 v/v), the eluent was acidified with a gradient of 0.10-0.2 mL of 4 M dioxane solution of HCl (per liter of eluent). The product-containing fractions were combined, filtered, and concentrated using a rotary evaporator to give 1.1 g (29%) of 1b as a white tetra·HCl salt. R$_f$(AcOH:H$_2$O:MeOH=3:6:1)=0.45. $^1$H NMR: δ 10.09 (s, NH, 2H), 9.71; (s, NH, 2H), 9.28; (s, NH, 2H), 7.94; (s, ArH, 4H), 6.88-6.60; (m, NH, 4H), 6.24-6.02; (m, NH$_2$, 4H), 3.97; (s, CCH$_2$, 4H), 3.46-3.22; (m, NHCH$_2$, 8H), 3.01; (t, J=2.5, CCH, 2H), 1.69-1.58; (m, CH$_2$CH$_2$, 8H). LR-ESI-MS (m/z) calculated for [M+H]$^+$: 599.4; found 599.2 HPLC (0.1% TFA in H$_2$O/MeOH (1:1, v/v), flow rate=3 mL/min): t=6.02 min (100%).

Using the general procedure described above, 0.3 g (0.9 mmol) of 7c and 0.6 g (1.9 mmol) of 9 afforded 0.5 g (65%) of 1c as a white tetra·HCl salt. $^1$H NMR: δ 10.13; (s, NH, 2H), 9.74; (s, NH, 2H), 9.32; (s, NH, 2H), 7.95; (s, ArH, 4H), 7.44-6.77; (m, NH, 8H), 3.47-3.26; (m, NHCH$_2$ and N$_3$CH$_2$, 16H), 1.74-1.57; (m, CH$_2$, 10H). LR-ESI-MS (m/z) calculated for [M+H]$^+$: 689.4; found 689.3. HPLC (0.1% TFA in H$_2$O/MeOH (1:1, v/v), flow rate=3 mL/min): t=5.95 min (100%).

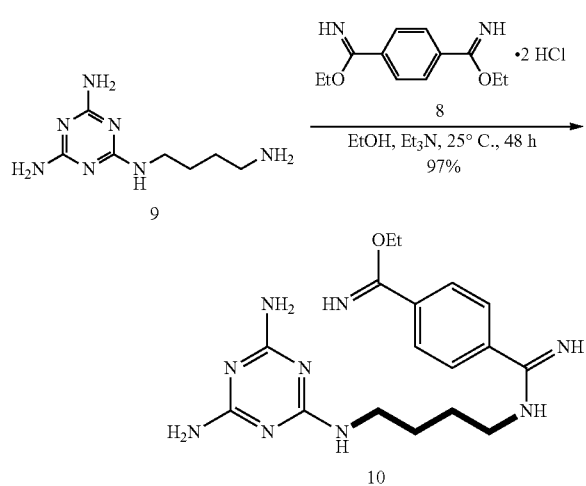

To a white suspension of 5.0 g (17.1 mmol) of 8 in 30 mL of anhydrous EtOH was added 7.5 mL (53.8 mmol) of Et$_3$N, resulting in a colorless clear solution. A solution of 1.1 g (5.7 mmol) of compound 9 {Arambula:2009ja} in 10 mL of EtOH was added dropwise over 8 h. The reaction mixture was stirred at room temperature for 48 h. The white solid was filtered, washed extensively with dichloromethane, dried under nitrogen overnight to give 2.1 g (97%) of compound 10 as a white solid. LR-ESI-MS (m/z) calculated for [M+H]$^+$: 372.2; found 372.2.

General Procedure for Preparation of Compounds 1d-f.

A suspension of 4.0 g (10.8 mmol) of 10 and 2.8 g (11.9 mmol) of 7a in 50 mL of anhydrous EtOH was stirred at room temperature overnight. The solvent was removed using a rotary evaporator. The resulting white solid was purified by silica gel column chromatography with a gradient mixture of CH$_2$Cl$_2$ and MeOH from 9:1 to 1:9 (v/v). After using 1 L of DCM/MeOH (1:9, v/v), the eluent was acidified with a gradient of 0.10-0.2 mL of 4 M dioxane solution of HCl (per liter of eluent). The product-containing fractions were combined, filtered, and concentrated using a rotary evaporator to give 5.4 g (71%) of 1d as a white tetra·HCl salt. $^1$H NMR: δ 10.11; (s, NH, 2H), 9.73; (s, NH, 2H), 9.30; (s, NH, 2H), 7.95; (s, ArH, 4H), 6.87-5.95; (m, NH and NH$_2$, 9H), 3.97; (s, CCH$_2$, 2H), 3.45; (t, J=7.1, NHCH$_2$, 4H), 3.25-3.21; (m, NHCH$_2$, 4H), 3.01; (t, J=2.4, CCH, 1H), 1.70-1.53; (m, CH$_2$, 8H). LR-ESI-MS (m/z) calculated for [M+H]$^+$; 561.3; found 561.4.

Using the general procedure described above, 0.3 g (0.8 mmol) of 10 and 5 mL (1.0 mmol) of 0.2 M ethanolic solution of 7b afforded 0.3 g (52%) of 1e as a white tetra·HCl salt, LR-ESI-MS (m/z) calculated for [M+H]$^+$, 575.4; found 575.5.

Using the general procedure described above, 3.5 g (9.4 mmol) of 10 and 2.9 g (10.4 mmol) of 7c afforded 4.3 g (61%) of 1f as a white tetra·HCl salt. $^1$H NMR: δ 10.13; (s, NH, 2H), 9.74; (s, NH, 2H), 9.32; (s, NH, 2H), 7.95; (s, ArH, 4H), 6.63-5.95; (m, NH and NH$_2$, 9H), 3.45; (t, J=7.2, NHCH$_2$, 4H), 3.38-3.54; (m, NHCH$_2$, 4H), 3.24-3.21; (m, NHCH$_2$ N$_3$CH$_3$, 4H), 1.74-1.53; (m, CH$_2$, 10H). LR-ESI-MS (m/z) calculated for [M+H]$^{3O}$: 606.4; found 606.2.

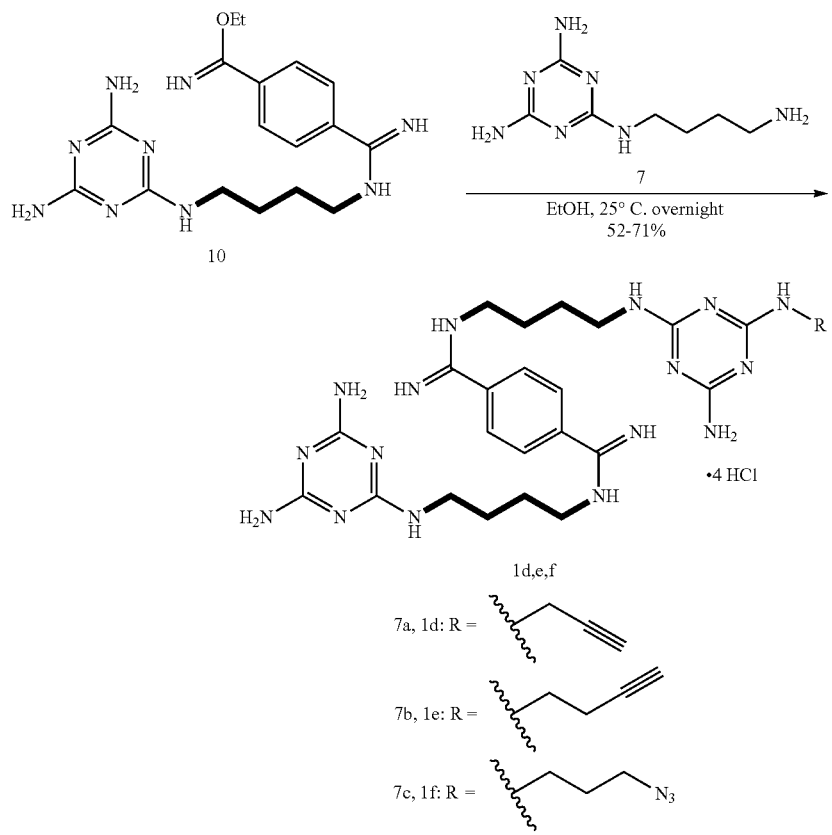

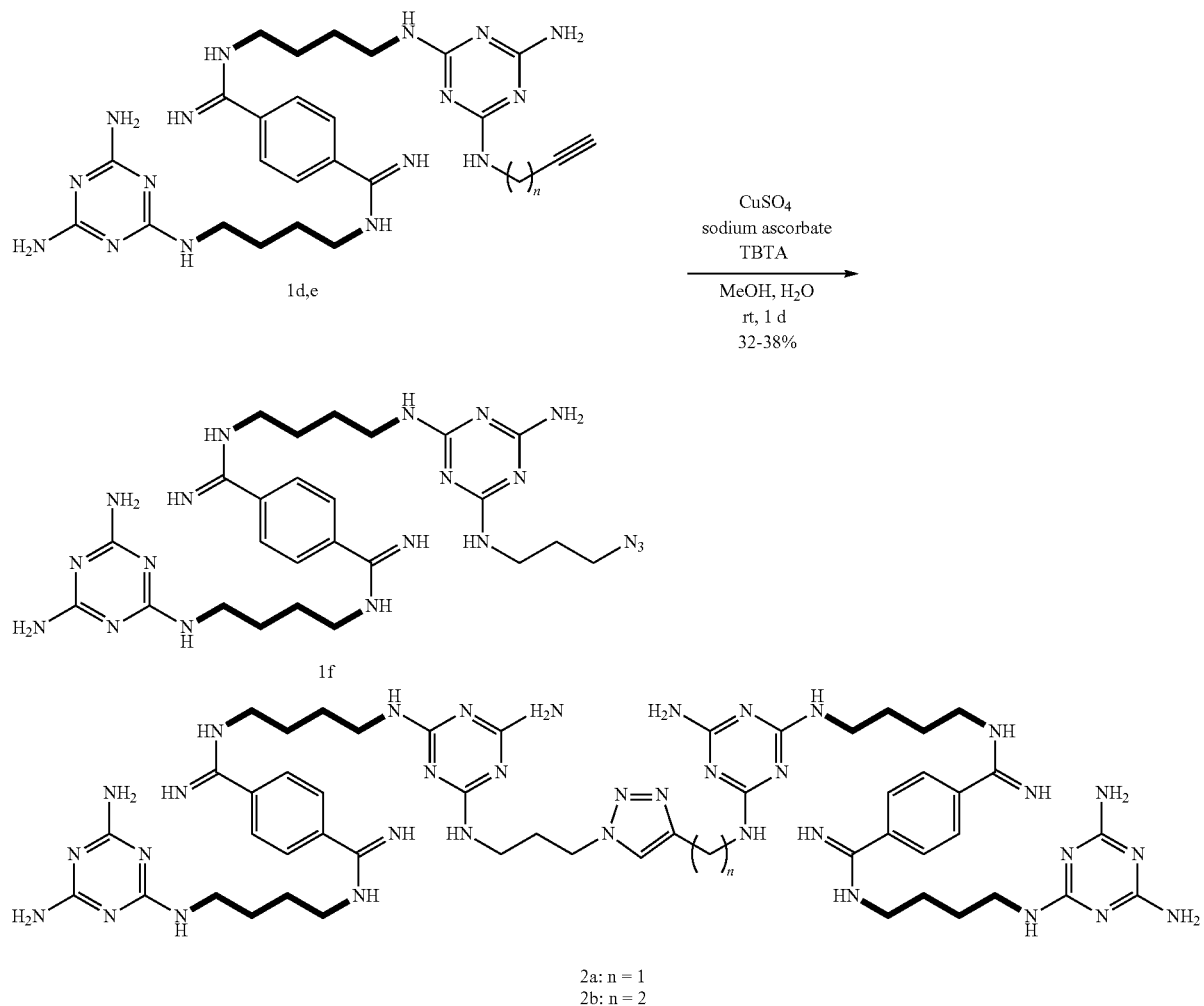

General Procedure for Preparation of Compounds 2a-b.

To a solution of 34 mg (0.049 mmol) 1d and 37 mg (0.049 mmol) of 1f in 11 mL of MeOH was added 148 μL (0.015 mmol) of 0.1 M DMSO solution of TBTA, 246 μL (0.025 mmol) of 0.1 M aqueous solution of copper sulfate. To the resulting solution was added 985 μL (0.099 mmol) of 0.1 M aqueous solution of sodium ascorbate. The mixture was stirred at room temperature for 24 h. Solvents were removed using a rotary evaporator. The resulting solid was suspended in 10 mL water. The suspension was filtered using a microfilter to obtain a clear solution. Concentrated aqueous hydrochloric acid solution was added to adjust to pH of the solution to 5-6. The resulting solution was loaded onto the Sephadex CM-25 column, and purified using an aqueous solution of ammonium bicarbonate from 0.1 M to 0.9 M. Fractions containing the product was collected, concentrated using a rotary evaporator at 60° C. The solid was dissolved in 5 mL of 1 M aqueous solution of hydrochloric acid. The resulting solution was frozen in an dry-ice bath, and dried in a lyophilizer for 2 days, gave 27 mg (38%) of 2a as a white solid. $^1$H NMR: δ 10.30; (s, NH, 4H), 9.83; (s, NH, 4H), 9.50-9.46; (m, NH, 4H), 8.58-7.86; (m, ArH and NH, 26H), 4.57-4.52; (m, CCH$_2$, 2H), 4.42-4.39; (m, NCH$_2$, 2H), 3.51-3.47; (m, NHCH$_2$, 8H), 3.38-3.27; (m, NHCH$_2$, 10H), 2.08-2.06; (m, CH$_2$, 2H), 1.72-1.59; (m, CH$_2$CH$_2$, 16H). $^{13}$C NMR: δ 161.61, 132.84, 128.70, 128.68, 47.08, 42.46, 29.52, 25.98, 24.61. LR-ESI-MS (m/z) calculated for [M+H]$^+$: 1166.7; found 584.0; ([M+2H]$^{2+}$, 35%), 389.7 ([M+3H]$^{3+}$, 60%), 292.6; ([M+4H]$^{4+}$, 100%).

Using the general procedure described above, 39 mg (0.054 mmol) of 1e and 40 mg (0.054 mmol) of 1f afforded 26 mg (32%) of 2b as a white solid: $^1$H NMR: δ 10.30; (s, NH, 4H), 9.83; (s, NH, 4H), 9.50-9.47; (s, NH, 4H), 8.51-7.87; (m, ArH and NH, 26H), 4.39; (t, J=7.2, NCH$_2$, 2H), 3.56-3.47; (m, NHCH$_2$, 10H), 3.36-3.26; (m, NHCH$_2$, 10H), 2.90-2.86; (m, CH$_2$, 2H), 2.07-2.04; (m, CH$_2$, 2H), 1.71-1.59; (m, CH$_2$CH$_2$, 16H). $^{13}$C NMR: δ 161.56, 155.70, 132.79, 128.63, 122.90, 47.01, 42.43, 25.93, 24.56. LR-ESI-MS (m/z) calculated for [M+H]$^+$: 1180.7; found 591.1; ([M+2H]$^{2+}$, 15%), 394.4; ([M+3H]$^{3+}$, 35%), 296.1; ([M+4H]$^{4+}$, 45%), 237.1; ([M+5H]$^{5+}$, 60%), 197.7; ([M+6H]$^{6+}$, 100%).

Example 2. Analytical Procedures, Drug Treatment, and Larval Crawling Assay

ITC, EMSA, confocal microscopy, IR splicing, and the reversal of rough-eye phenotype assays were conducted as previously described (Wong et al., *J. Am. Chem. Soc.* 2014, 136, 6355-6361). The cytotoxicity of 2a was accessed using a published protocol (Vichai et al., Sulforhodamine B colorimetric assay for cytotoxicity screening, *Nat. Protoc.* 2006, 1, 1112-1116).

Isothermal Titration Calorimetry (ITC) Studies.

The ligand stock solution (10 mM in water). MOPS buffer (100 mM; pH 7.0±0.2), and NaCl (5000 mM) were prepared. The ligand solution (1 mL) contained of 0.5 mM of ligand, 20 mM of MOPS buffer, and 150 mM of NaCl. The RNA solution (2 mL) contained 0.02 mM of RNA, 20 mM of MOPS buffer, and 150 mM of NaCl. The resulting RNA solution was heated in a water bath at 90° C. for 5 min, then allowed to cool to room temperature for 2 h.

ITC measurements were performed at 25° C. on a Micro-Cal VP-ITC calorimeter (Northampton, Mass.). A typical experiment consisted of titrating 10 µL of a ligand solution (500 µM) from a 250 µL syringe (stirred at 300 rpm) into a sample cell containing 1.42 mL of a RNA solution (10 µM) with total 28 injections. The initial delay prior to the first injection was 60 s. The duration of each injection was 24 s and the delay between injections was 300 s. Data analysis was carried out with Origin 5.0 software (MicroCal). Binding parameters such as the dissociation constant ($K_D$), enthalpy change ($\Delta H$), and entropy change ($\Delta S$) were determined by fitting the experimental binding isotherms with various model.

Figure 5A:
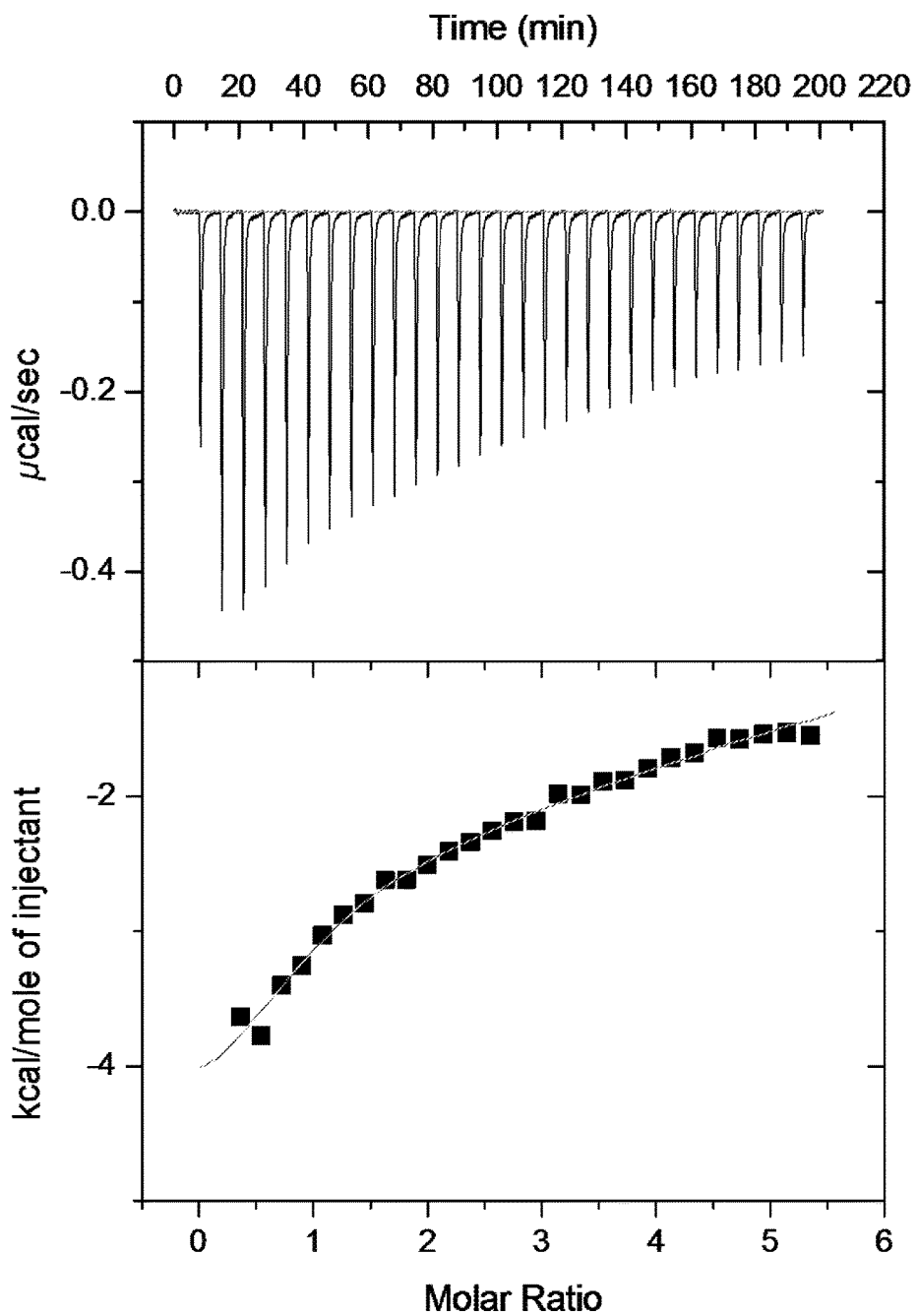
FIG. 5A-B. ITC binding isotherms to $(CUG)_{12}$ for compounds 1b(A) and 1c(B). The binding isotherms were best fitted with 3 sequential binding sites model using Origin. The highest association constant for 1b is $K_A=1.3\times10^5\pm2.7\times10^4$. The highest association constant for 1c is $K_{A1}=2.1\times10^5\pm5.2\times10^4$.
Figure 5B:
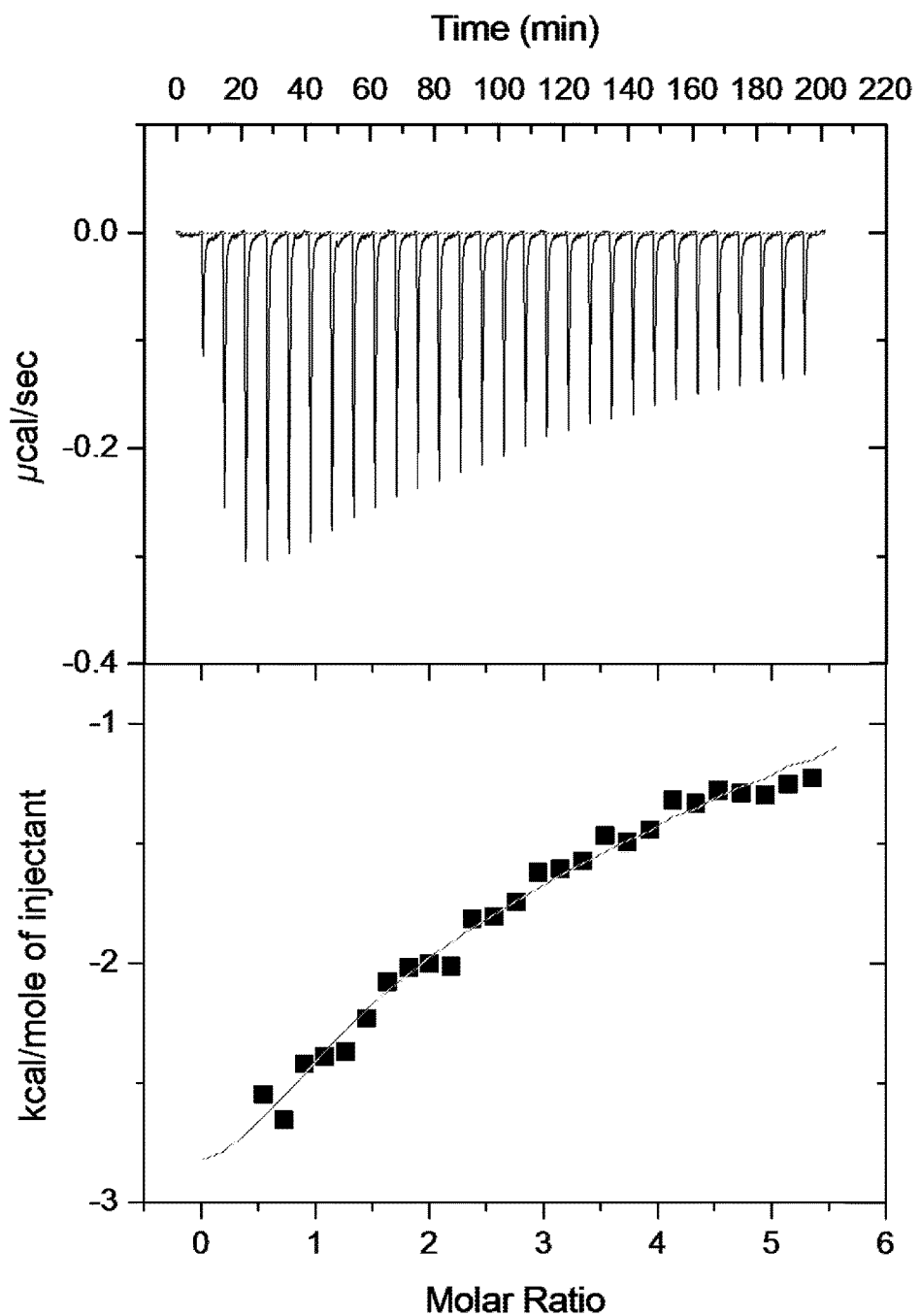

The results are shown in FIG. 5A-B (ITC binding isotherm to $(CUG)_{12}$ of 1b (5A) and 1c (5B). The binding isotherm was best fitted with the 3 sequential binding sites model using Origin. The highest association constants for 1b are $K_A = 1.3 \times 10^5 \pm 2.7 \times 10^4$. The highest association constants for 1c are $K_{A1} = 2.1 \times 10^5 \pm 5.2 \times 10^4$.

Determination of Dissociation Constant ($K_D$) of the MBNL1-$(CUG)_{16}$ Complex by EMSA.

Figure 6:
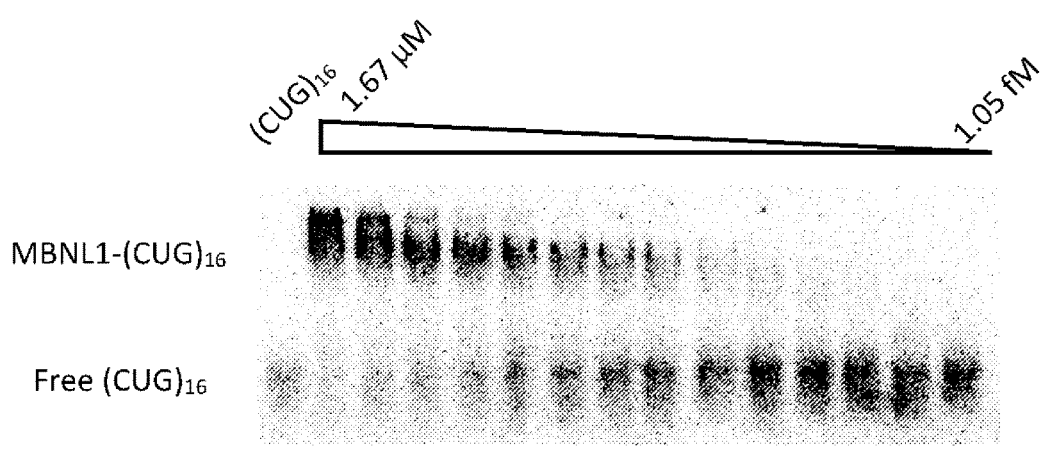
FIG. 6. Determination of the dissociation constant ($K_D$) of the MBNL1-$(CUG)_{16}$ complex by EMSA. The concentration of the protein was serially diluted by a factor of 3 from 1.67 µM to 1.05 fM. The concentration of $(CUG)_{16}$ was 0.2 nM.
Figure 7:
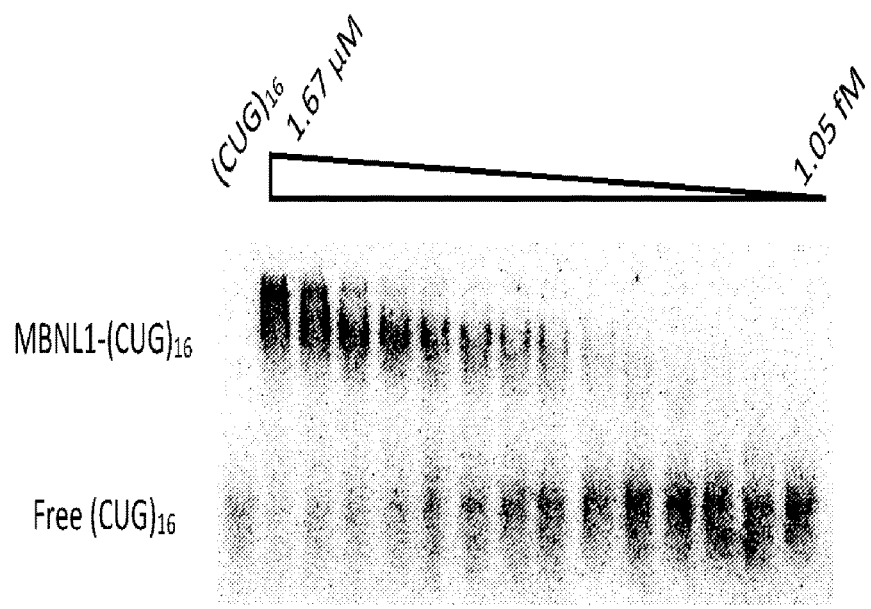
FIG. 7. Determination of the dissociation constant ($K_D$) of the MBNL1-$(CUG)_{16}$ complex by ESMA. The $K_D$ (1:1 stoichiometry assumption) was obtained by fitting the normalized fraction RNA bound versus the concentration of protein using the equation: Fraction RNA bound=$B_{max} \times [\text{MBNL1}]_{total}^h/(K_D^h+[\text{MBNL1}]_{total}^h)$ where $B_{max}$ is maximum fraction RNA bound, and h is a Hill slope.

$(CUG)_{16}$ RNA was labeled with $[\gamma\text{-}^{32}P]$-ATP using T4 poly-nucleotide kinase (New England Biolabs). Labeled RNA was purified by phenol extraction and ethanol precipitation. Labeled RNA was heated at 95° C. for 5 min, then placed on ice for 10 min and diluted in protein binding buffer (175 mM NaCl, 5 mM $MgCl_2$, 20 mM Tris-HCl (pH 8), 1.25 mM 2-mercapto-ethanol (BME), 12.5% glycerol, 2 mg/ml bovine serum albumin (BSA), 0.1 mg/ml heparin, 0.05% or 0.1% Triton X). For MBNL1-$(CUG)_{16}$ binding study, MBNL1 was serially diluted by a factor of 3 in protein binding buffer. To each solution was added labeled RNA, so that the final concentration of RNA was 0.2 nM. The resulting mixtures were incubated at room temperature for 10 min and loaded onto a 6% polyacrylamide gel (80:1) at 4° C. The gel was run for 2 h at 180 V in Tris-Borate 0.5× buffer (pH 8.2-8.3). Gels were dried at 80° C. under high vacuum for 2 h, developed overnight in phosphor exposure cassette, and visualized on a Molecular Dynamics Storm PhosphorImager. The $K_D$ (1:1 stoichiometry assumption) was obtained by fitting the normalized fraction RNA bound versus the concentration of protein using the equation:

$$\text{Fraction RNA bound} = B_{max} \times [\text{MBNL1}]_{total}^h / (K_D^h + [\text{MBNL1}]_{total}^h)$$

where $B_{max}$ is maximum fraction RNA bound, h is a Hill slope. Protein concentration in reaction mixture was larger than 10-fold excess over RNA concentration. Data is illustrated in FIGS. 6 and 7.

Drug Treatment in *Drosophila*.

*Drosophila* lines were cultured in standard cornmeal medium supplemented with dry yeasts. Fly lines bearing UAS-(CTG)60 and UAS-(CTG)480 were kind gifts of Prof. Rubén Artero Allepuz (Universitate de Valéncia, Estudi General, Spain). The gmr-GAL4 and 23B-GAL4 lines were used to drive UAS transgene expression in eye and muscles respectively. Ligands 1a and 2a were dissolved in $ddH_2O$ and mixed with fly food. Genetic crosses were set up in drug-containing fly food at 21.5° C. for external eye assay, and at 25° C. for larval crawling assay.

Larval Crawling Assay.

Larval crawling assay was performed as previously described (Lanson et al., *Hum. Mol. Genet.* 2011, 20, 2510-2523). Ten wandering third instar larvae were washed in $ddH_2O$ and placed on a 2% agarose gel in a 15-cm Petri dish with gridlines spaced at 0.5 cm. The larvae were allowed to acclimate for a period of 1 min, and the total number of gridlines that the posterior end of the larvae passes in 1 min was determine. Each set of experiment was repeated independently for three times using larvae collected from separate genetic crosses.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |

| (iv) Injection 1 (1 mg/mL) | mg/mL |
|---|---|
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventionally procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

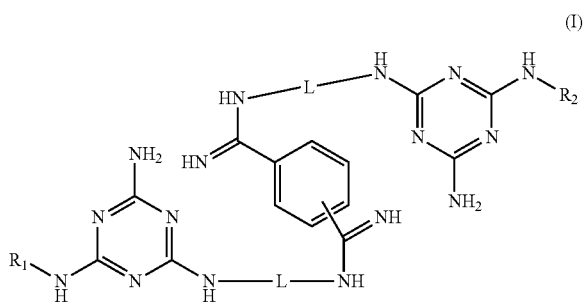

wherein $R^1$ is H, —$(C_1$-$C_5)$alkyl-C≡CH, or —$(C_1$-$C_5)$alkyl-$N_3$;

$R^2$ is H, —$(C_1$-$C_5)$alkyl-C≡CH, —$(C_1$-$C_5)$alkyl-$N_3$, or a moiety of Formula IA:

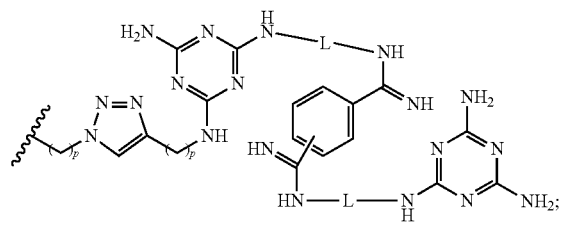

(IA)

wherein
each p is independently 1-8; and
each L is independently —(C$_3$-C$_5$)alkylene-, —(C$_2$-C$_5$) alkylene- interrupted by one oxygen, 1,3-cyclopenylene, 1,3-cyclohexylene, or 1,4-cyclohexylene; provided that one of R$^1$ and R$^2$ is not H;
or a salt or solvate thereof.

2. The compound of claim 1 wherein R$^1$ is H, propargyl, -ethyl-C≡CH, -propyl-C≡CH, -ethyl-N$_3$, -propyl-N$_3$, or -butyl-N$_3$.

3. The compound of claim 1 wherein R$^2$ is H, propargyl, -ethyl-C≡CH, -propyl-C≡CH, -ethyl-N$_3$, -propyl-N$_3$, or -butyl-N$_3$.

4. The compound of claim 1 wherein R$^1$ is H and R$^2$ is propargyl or —CH$_2$CH$_2$—C≡CH.

5. The compound of claim 1 wherein R$^1$ is H and R$^2$ is —(C$_2$-C$_4$)alkyl-N$_3$.

6. The compound of claim 1 wherein R$^1$ and R$^2$ are each propargyl or —CH$_2$CH$_2$—C≡CH.

7. The compound of claim 1 wherein R$^1$ and R$^2$ are each —(C$_2$-C$_4$)alkyl-N$_3$.

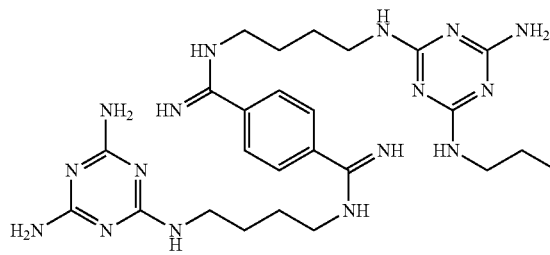

8. The compound of claim 1 wherein R$^2$ is a moiety of Formula IA and R$^1$ is H, —(C$_1$-C$_4$)alkyl-C≡CH, or —(C$_1$-C$_4$)alkyl-N$_3$.

9. The compound of claim 8 wherein R$^1$ is H.

10. The compound of claim 8 wherein each p is independently 1, 2, or 3.

11. The compound of claim 8 wherein each L of the moiety of Formula IA is propylene, butylene, or pentylene.

12. The compound of claim 1 wherein the substituents on the central phenyl ring of Formula I are in a para orientation.

13. The compound of claim 1 wherein each L of the compound of Formula I or the moiety of Formula IA, independently of one another, is propylene, butylene, or pentylene.

14. The compound of claim 1 that is a compound of Formula II:

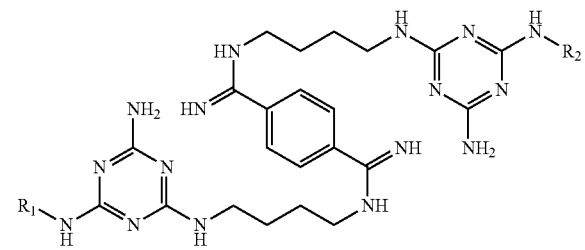

(II)

wherein R$^1$ and R$^2$ are each independently propargyl, —CH$_2$CH$_2$—C≡CH, or —CH$_2$CH$_2$CH$_2$—N$_3$; or a salt or solvate thereof.

15. The compound of claim 1 that is a compound of Formula II:

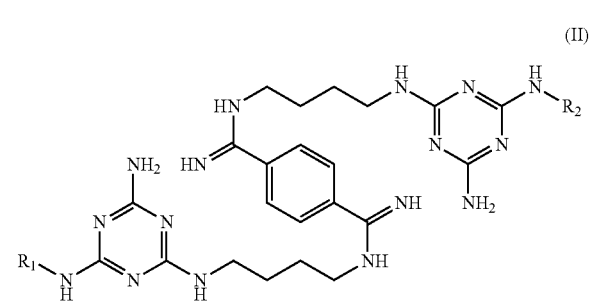

(II)

wherein R$^1$ is H and R$^2$ is propargyl, —CH$_2$CH$_2$—C≡CH, or propyl-N$_3$; or a salt or solvate thereof.

16. The compound of claim 1 wherein the compound is:

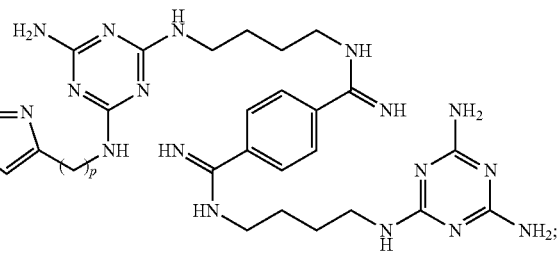

wherein p is 1 or 2; or a salt or solvate thereof.

17. A pharmaceutical composition comprising the compound claim 1 in combination with a pharmaceutically acceptable diluent, carrier, or excipient.

18. A method of reducing the symptoms of myotonic dystrophy comprising administering to a patient having myotonic dystrophy an effective amount of a compound of claim 1, thereby reducing the symptoms of the myotonic dystrophy.

19. The method of claim 18 wherein the myotonic dystrophy is myotonic dystrophy type 1 (DM1).

20. The method of claim 18 wherein the symptoms of myotonic dystrophy reduced by the administration are one or more of myopathy, myotonia, progressive muscle atrophy, cataracts, cardiac defect, and insulin dependent diabetes.

21. A compound of Formula I:

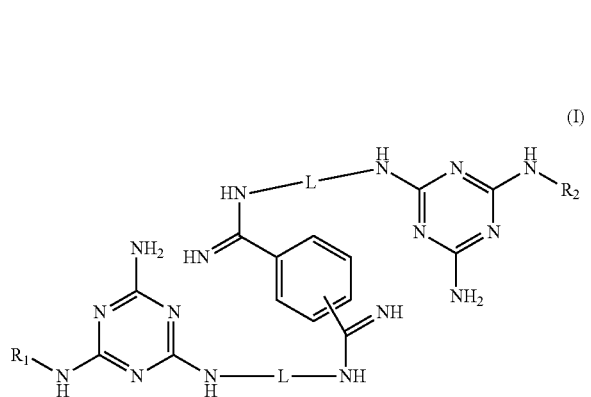

wherein
R$^1$ is H, —(C$_1$-C$_5$)alkyl-C≡CH, or —(C$_1$-C$_5$)alkyl-N$_3$;

R$^2$ is a moiety of Formula IA:

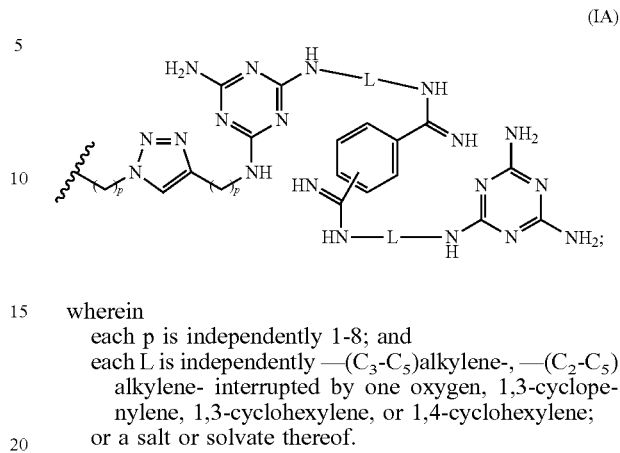

wherein
each p is independently 1-8; and
each L is independently —(C$_3$-C$_5$)alkylene-, —(C$_2$-C$_5$) alkylene- interrupted by one oxygen, 1,3-cyclopenylene, 1,3-cyclohexylene, or 1,4-cyclohexylene;
or a salt or solvate thereof.

22. A method of reducing the symptoms of myotonic dystrophy comprising administering to a patient having myotonic dystrophy an effective amount of a compound of claim 21, thereby reducing the symptoms of the myotonic dystrophy.

* * * * *

UNITED STATES PATENT AND TRADEMARK OFFICE
CERTIFICATE OF CORRECTION

PATENT NO.        : 10,266,520 B2
APPLICATION NO.   : 15/502474
DATED             : April 23, 2019
INVENTOR(S)       : Paul J. Hergenrother Page 1 of 1

It is certified that error appears in the above-identified patent and that said Letters Patent is hereby corrected as shown below:

- In Claim 1, at Lines 65-66:
Please remove:
"$R^1$ is H, -($C_1$-$C_5$)alkyl-C≡CH, or-($C_1$-$C_5$)alkyl-$N_3$;
$R^2$ is H, -($C_1$-$C_5$)alkyl-C≡CH, -($C_1$-$C_5$)alkyl-$N_3$, or"
And insert:
-- $R^1$ is H, -($C_1$-$C_8$)alkyl-C≡CH, or-($C_1$-$C_8$)alkyl-$N_3$;
$R^2$ is H, -($C_1$-$C_8$)alkyl-C≡CH, -($C_1$-$C_8$)alkyl-$N_3$, or -- therefore.

- In Claim 21, at Line 26:
Please remove:
"$R^1$ is H, -($C_1$-$C_5$)alkyl-C≡CH, or-($C_1$-$C_5$)alkyl-$N_3$;"
And insert:
-- $R^1$ is H, -($C_1$-$C_8$)alkyl-C≡CH, or-($C_1$-$C_8$)alkyl-$N_3$; -- therefore.

Signed and Sealed this
Fourth Day of June, 2019

Andrei Iancu
*Director of the United States Patent and Trademark Office*